US006265413B1

(12) United States Patent
Jew et al.

(10) Patent No.: US 6,265,413 B1
(45) Date of Patent: *Jul. 24, 2001

(54) CAMPTOTHECIN COMPOUNDS AND A METHOD OF PREPARATION THEREOF

(75) Inventors: Sang Sup Jew, Seoul; Hee Soon Lee, Cheongju; Joon Kyum Kim, Seoul; Kwang Dae Ok, Suwon; Kyeong Hoi Cha, Kwangmyeong; Myoung Goo Kim, Seoul; Kwang Kyun Lee, Seoul; Jong Min Kim, Seoul; Hee Jin Kim, Pusan; Jeong Mi Hah, Seoul, all of (KR)

(73) Assignee: Chong Kun Dang Corp., Seoul (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,655

(22) PCT Filed: Jan. 9, 1996

(86) PCT No.: PCT/KR96/00004

§ 371 Date: Jul. 7, 1997

§ 102(e) Date: Jul. 7, 1997

(87) PCT Pub. No.: WO96/21666

PCT Pub. Date: Jul. 18, 1996

(30) Foreign Application Priority Data

Jan. 9, 1995 (KR) ..................................................... 95-269

(51) Int. Cl.[7] ..................................................... A61K 31/44

(52) U.S. Cl. ............................. 514/283; 514/279; 546/41

(58) Field of Search ............................... 546/41; 514/283, 514/279

(56) References Cited

U.S. PATENT DOCUMENTS 4,894,456 1/1990 Wall et al. ............................. 546/41

FOREIGN PATENT DOCUMENTS 0 074 770 3/1983 (EP) .
0 088 642 9/1983 (EP) .
0 540 099 A1 5/1993 (EP) .
92/05785 4/1992 (WO) .

OTHER PUBLICATIONS

Journal of Medicinal Chemistry, vol. 34, pp. 98–107 (1991).
Arch. Pharma. (Weinheim) vol. 316, No. 8, pp. 707–712 (1983) Abstract Only.
Journal of Medicinal Chemistry, vol. 36, No. 18, pp. 2689–2700 (1993).
English Abstract of JP 6–228141, 1994.*
Xie, Bioorg. Med. Chem. Lett. 5, 2189, 1995.*
Monroe E. Wall et al., "The Isolation and Structure of Camptothecin, a Novel Alkaloidal Leukemia and Tumor Inhibitor from *Camptotheca acuminata"*, Journal of the American Chemical Society, pp. 3888–3890, Aug. 20, 1966.
Robert T. Crow et al., "Structural Modifications of Camptothecin and Effects on Topoisomerase I Inhibition", Journal of Medicinal Chemistry, vol. 35, No. 22, pp. 4160–4164, 1992.

* cited by examiner

*Primary Examiner*—Christopher S. F. Low
*Assistant Examiner*—David Lukton
(74) *Attorney, Agent, or Firm*—Finnegan, Henderson, Farrabow, Garrett & Dunner L.L.P.

(57) ABSTRACT

Camptothecin derivatives and pharmaceutically acceptable salts thereof, its manufacturing method and an antineoplastic agent containing it. The camptothecin derivatives are modified in B-ring and E-ring and show improved water solubility and enhanced antineoplastic effect.

3 Claims, 2 Drawing Sheets

CAMPTOTHECIN COMPOUNDS AND A METHOD OF PREPARATION THEREOF

TECHNICAL FIELD

This invention relates to camptothecin derivatives and pharmaceutically acceptable salts thereof, expressed by the following chemical formula (I), its manufacturing method and antineoplastic agent containing it as an active ingredient (I)

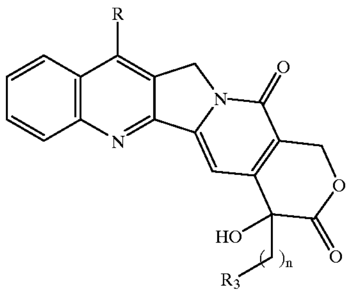

Wherein;

R is hydrogen or $—(CH_2)_2—NR_1R_2$, ($R_1$ is hydrogen or a general protecting group of amine; $R_2$ is a lower alkyl, hydroxyethyl or acetoxyethyl; further, $R_2$ may form heterocyclic compound by binding with an adjacent nitrogen);

n is 1 or 2; $R_3$ is hydrogen or $—OR_4$ [$R_4$ is hydrogen or

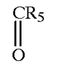

($R_5$ is methyl or $CH_3OCH_2—$);

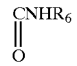

($R_6$ is isopropyl, phenyl or $—CH_2CH_2Cl$.); $CH_2OR_7$ ($R_7$ is methyl, ethyl or $CH_3OCH_2CH_2—$)];

Wherein;

When n is 2 and $R_4$ is hydrogen, R is not hydrogen;

and when n is 2 and $R_3$ is H, R is not hydrogen;

also, when R is $—CH_2CH_2NHCH_3$, $R_3$ is not hydrogen.

BACKGROUND OF ART

Since the isolation of camptothecin from the Chinese tree, *Camptotheca acuminata,* by Wall and co-workers (J. Am. Chem. Soc., 1966, 88, 3888), there had been many approaches to synthesize camptothecin. However, the development of camptothecin as an effective antineoplastic agent was unsuccessful due to its severe toxicity in the first clinical trial in 1970.

Thereafter, Liu et al. reported in 1985 that camptothecin had a specific mode of action to inhibit topoisomerase I. Thus, considerable interest has focused on this compound. In particular, since topoisomerase I inhibitor itself was not used clinically, it is expected that with its actual development, camptothecin may be very efficiently used in combination with other antineoplastic chemotherapeutics having different modes of action.

Recently, various studies for the development of camptothecin derivatives have been proposed in order to reduce the toxicity of camptothecin and to further enhance its antineoplastic activities. Among these related studies, the clinical trial of CPT-11 (Irinotecan) synthesized by Yakurt-Honsha Co. of Japan in 1986 showed that it exhibited excellent antineoplastic activities with less toxicity (Japanese Patent Laid Open Publication No. 64-61482) and followed by other pharmaceutical companies such as Smithkline Beecham (Topotecan) and Glaxo (MDO-camptothecin and 9-aminocamptothecin). Among them, CPT-11 is launched. In particular, it is noticeable that said CPT-11 compound has exhibited excellent antineoplastic activities in the treatment of incurable solid tumors such as the lung cancer.

Since a majority of camptothecin derivatives developed hitherto were semi-synthetic compounds which were obtained from the chemical modification of camptothecin, there were some difficulties in procuring camptothecin and in developing derivatives with a variety of structures because of restrictions of said chemical modification. In addition, these reported total synthesis are not satisfactory in view of both chemical and optical yields.

DISCLOSURE OF INVENTION

Accordingly, the inventor et al. have confirmed that through the total synthesis for a series of novel compounds expressed by said general formula (I) and followed by in vitro test, these compounds with different mode of action may be used as effective antineoplastic agents. Thus, the present invention has been completed.

Camptothecin is a fused ring system, composed of a quinoline (A and B), fused to a pyrrolidine ring (C), fused to an alpha-pyridone ring (D) which in turn is fused to a lactone ring(E).

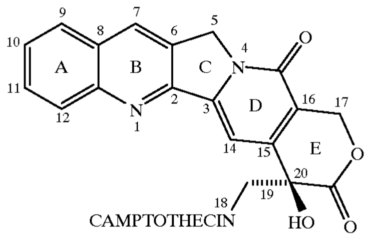

CAMPTOTHECIN

In particular, further careful review has been made on camptothecin's mode of action to inhibit topoisomerase I and various structures of camptothecin derivatives developed hitherto, and attempts have been also made in such a manner to modify the substituents of B-ring or E-ring in camptothecin.

In consideration of the fact that the conventionally developed derivatives have suffered from some side effects such as nausea, vomiting and cystitis due to extremely poor water solubility, the introduction of side chain at B-ring of camptothecin was made in such a manner that in order to enhance the solubility. Hence, the side chain including amino groups was introduced at the 7-position of camptothecin.

In view of the mode of action suggested by Crow that camptothecin binds covalently with topoisomerase I [*J. Med. Chem.,* 1992, 35, 4160–4164], the modification of camptothecin at E-ring was attempted so as to enhance its reactivity.

The processes for manufacturing camptothecin derivatives and its intermediates are described in more detail as set forth hereunder, in accordance with the practice of this invention.

The compounds based upon EXAMPLES can be prepared in accordance with the practice of this invention as specified in the following Scheme 1.

Scheme 1

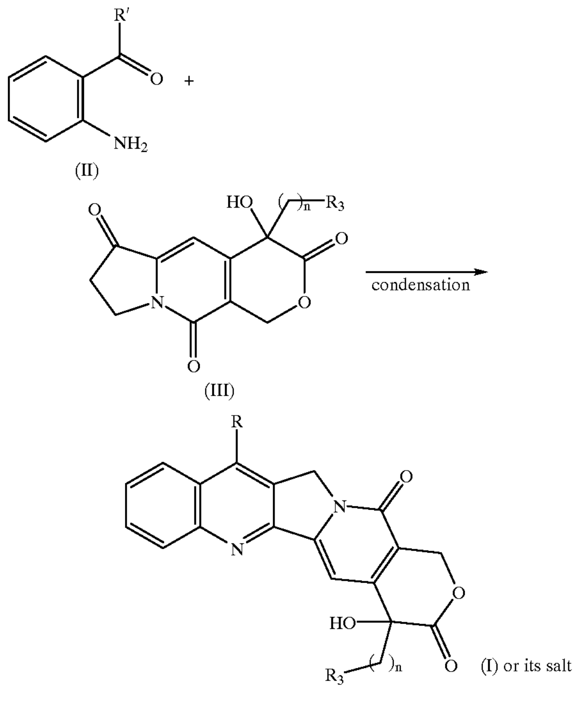

(II)

(III)

(I) or its salt

Wherein;

R, n and $R_3$ are the same as described in the above and R' is hydrogen or —$(CH_2)_2$—$NR_1R_2$; $R_1$ is a general protecting group of amine; $R_2$ is the same as described in the above. Friedlander condensation of aminoketone compound (II) with tricyclic Ketone (III) affords the compound expressed by the general formula (I) [organic reactions, 28, 37–202, Wiley & Sons Inc, New York (1932)].

The condensation of the compounds (II) and (III) is conducted, in general, in the presence of acid at room temperature or under the heating condition.

The following inert solvents should be used for the reactions so as not to affect the reactions, for example, aromatic hydrocarbons(toluene, benzene, xylene etc.), hydrocarbon halide(dichloromethane, chloroform, 1,1-dichloroethane, 1,2-dichoroethane etc.), lower alcohols, amides (N,N-dimethylformamide etc.), or acetic acid.

The reactions may be conducted using inorganic acid (hydrochloric acid or sulfuric acid) or organic acids (methanesulfonic acid, trifluoromethanesulfonic acid, ρ-toluenesulfonic acid, acetic acid, etc.).

The reaction time ranges from 1 to 48 hrs, and the reaction temperature is 30 to 150° C.

As a typical reaction condition, it is most preferable that reflux is made available in the presence of ρ-toluenesulfonic acid in toluene.

When R is —$CH_2CH_2NHR_2$ ($R_1$ is hydrogen) in the synthesis of general formula (I), said amino protecting group is removed through the catalytic hydrogenation using platinum or palladium.

When R' is hydrogen in the compound (II), compound(I) is obtained after carbonyl group of the compound(II) is protected by acetalization with ethylene glycol or by formation of shiff base with ρ-toluidine according to known process. [Chem. Ber. 76, 1099(1943)].

When $R_3$ is hydroxy group in the compound (III), thus obtained compound(I), wherein $R_3$ is hydroxy group, is reacted with such reagents as

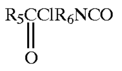

and $R_7OCH_2Cl$ to produce the compound(I) wherein the hydroxy group of $R_3$ is thus modified.

In particular, when $R_6NCO$ is used, the compound expressed by the general formula (I) can be obtained by using the catalytic amounts of tin complex (e.g., di-n-butyltin diacetate, etc.).

The aminoketone (II) can be prepared in accordance with Scheme 2.

Scheme 2

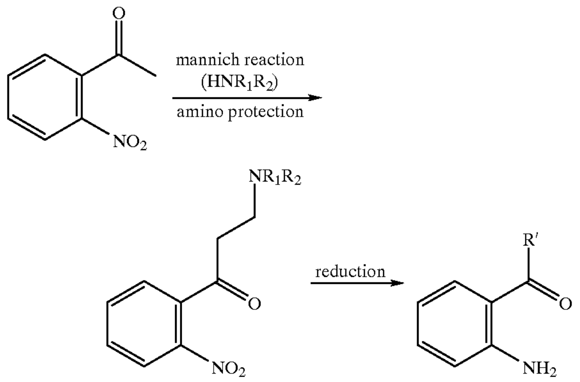

(IV)

(II)

Wherein;

R', $R_1$ and $R_2$ are the same as described in the above.

A novel aminoketone compound (II) of this invention can be prepared as follows:

2'-nitroacetophenone reacts with monoalkylamine (e.g., ethylamine, propylamine or isopropylamine), monoarylamine (e.g., benzylamine) or dialkylamine (e.g., morpholine, piperidine or diethylamine) in the presence of conc. hydrochloric acid, through Mannich reaction with paraformaldehyde to give the compound (IV).

The reaction is conducted at 30–80C for 1 to 48 hrs.

In case of the compound (IV) having monoalkylamine or monoarylamine, the general protecting group of amine is introduced to give the said compound (IV).

According to this invention, Cbz (carbobenzyloxy) is a preferable protecting group of amine.

The compound (IV) is treated with sodium dithionite in lower alcohol solvent to give the compound (II).

The reaction is conducted at 30 to 100° C. for 1 to 10 hrs.

As specified in Scheme 3 below, a novel tricyclic ketone (III) of this invention can be prepared from the compound (IX) which is already known.
From the compound (III), tricyclicketone (n is 2 and $R_3$ is H) is already known compound prepared in accordance with a convention method (U.S. Pat. No. 4,894,456 (1990)).
Scheme 3
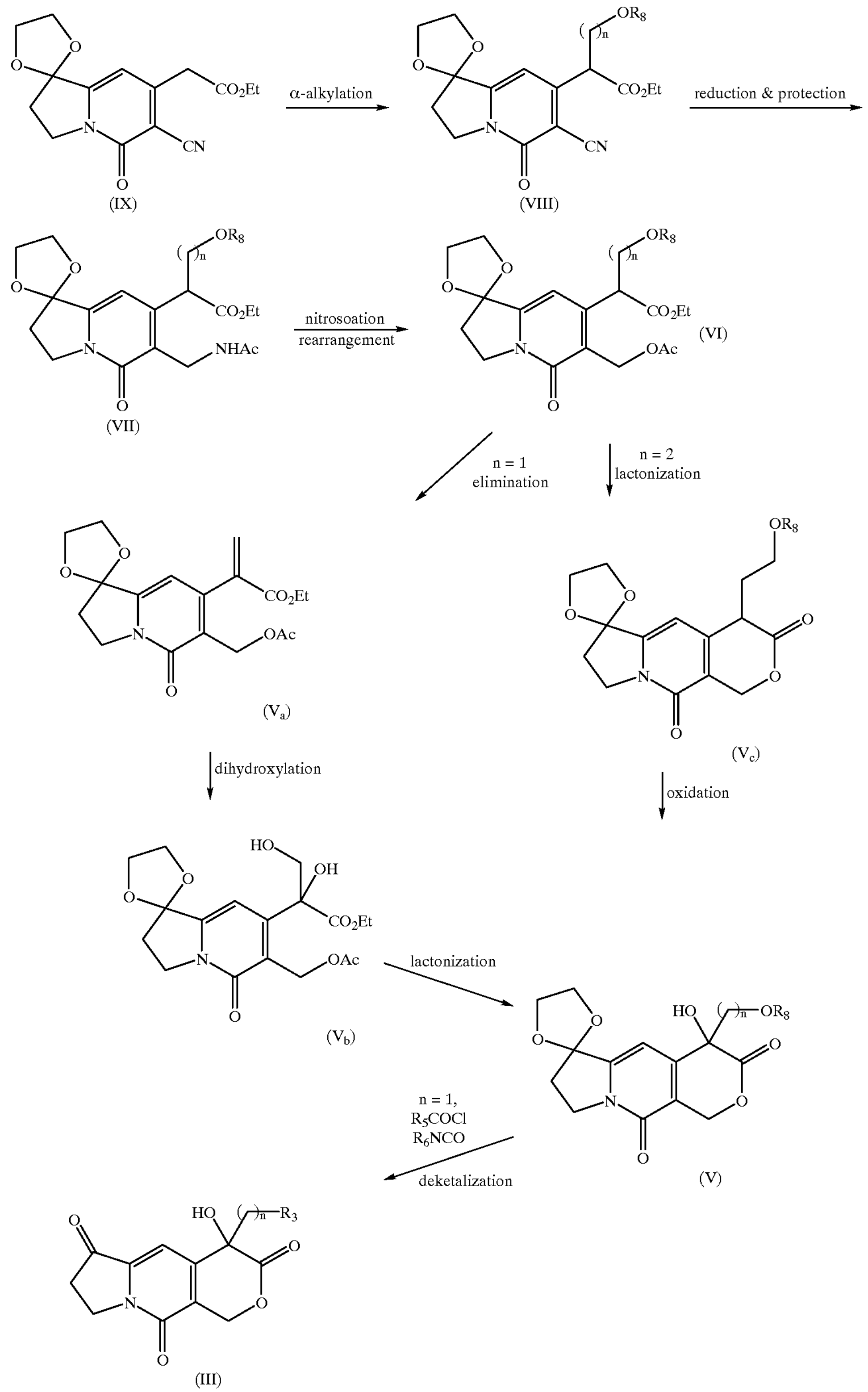
(IX) (VIII) (VII) (VI) ($V_a$) ($V_c$) ($V_b$) (V) (III)

Wherein;

$R_3T$ n, $R_5$ and $R_6$ are the same as described in the above and $R_8$ is the general protecting group of hydroxyl group.

During α-alkylation re action where n is 2, the compound (IX) reacts with base such as KOtBu or NaH in inert solvent including N, N-dimethylformamid or 1,2-dimethoxyethane. Then, the reaction mixture is reacted with 2-bromoethanol protected with tetrahydropyranyl, methoxymethyl or methoxyethoxymethyl to give the compound (VIII).

The reaction is preferably conducted at 30 to 60° C. for 18 to 48 hrs.

Meanwhile, when n is 1, α-hydroxymethylation is conducted using formaldehyde in alcoholic solvent and followed by the protection with the general protecting group of OH to give the compound(VIII).

The preferable protecting group of this invention is methoxymethyl or methoxyethoxymethyl.

The compound (VII) was obtained by the reduction of compound (VIII) using Raney-Nickel as a catalyst in a cosolvent of acetic acid and acetic anhydride.

The reaction is conducted at 30 to 80° C. for 1 to 10 hrs.

The rearrangement via nitroso compound is done by reacting the compound (VII) with sodium nitrite in a co-solvent of acetic anhydride and acetic acid at 0 to 50° C. for 1 to 24 hrs. Thus, obtained nitroso compound is refluxed in the solvent such as CCl4 at 60 to 90° C. for 5 to 18 hrs to give the compound (VI).

When n is 1 or 2, the reaction route of the diester (VI) becomes slightly different. In case that n is 2, compound(VI) is hydrolyzed in alkali aqueous solution including LiOH, NaOH and KOH in methanol and treated with acidic aqueous solution such as acetic acid or hydrochloric acid to give the compound (Vc).

Said hydrolysis is conducted at 0 to 50° C. for 30 mins to 5 hrs.

The lactonization in acidic aqueous solution is conducted at 0 to 50° C. for 1 to 48 hrs.

Compound (Vc) is treated with base such as potassium t-butoxide in the amine solvents such as N,N-dimethylformamide or N,N-dimethylacetamide and oxidized with the bubbling of $O_2$ under triethylphosphite to give the compound (V).

The reaction is conducted at −10 to 50° C. for 30 mins to 5 hrs.

Meanwhile, when n is 1, compound(VI) is treated with organic base such as DBU, DBN or triethylamine in aromatic hydrocarbon solvent such as benzene, toluene or xylene to produce the compound (Va).

The reaction is conducted at 0° C. to 100° C. for 10 mins to 5 hrs.

The compound (Va) is treated with $OsO_4$ in a pyridine solvent to give the compound (Vb). This reaction is conducted at 10 to 50° C. for 1 to 10 hrs. The lactonization of the compound (Vb) is carried out as the same as described in the above.

The compound (V) where n is 2, is treated with acid to produce compound (III). The reaction is conducted at 10 to 80° C. for 30 mins to 10 hrs. In case of the compound (V) wherein n is 1, said deketalization is done after introducing the substituent by treating

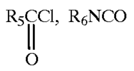

for the preparation of the compound (III).

In case of the compound (I) of this invention where R is $CH_2CH_2NR_1R_2$, the conversion of secondary amine into the salts of inorganic acids (e.g., hydrochloric acid, sulfuric acid, phosphoric acid, etc.) or organic acids (e.g., acetic acid) makes it possible to prepare physiologically acceptable salts.

BEST MODE FOR CARRYING OUT THE INVENTION

Figure 1:
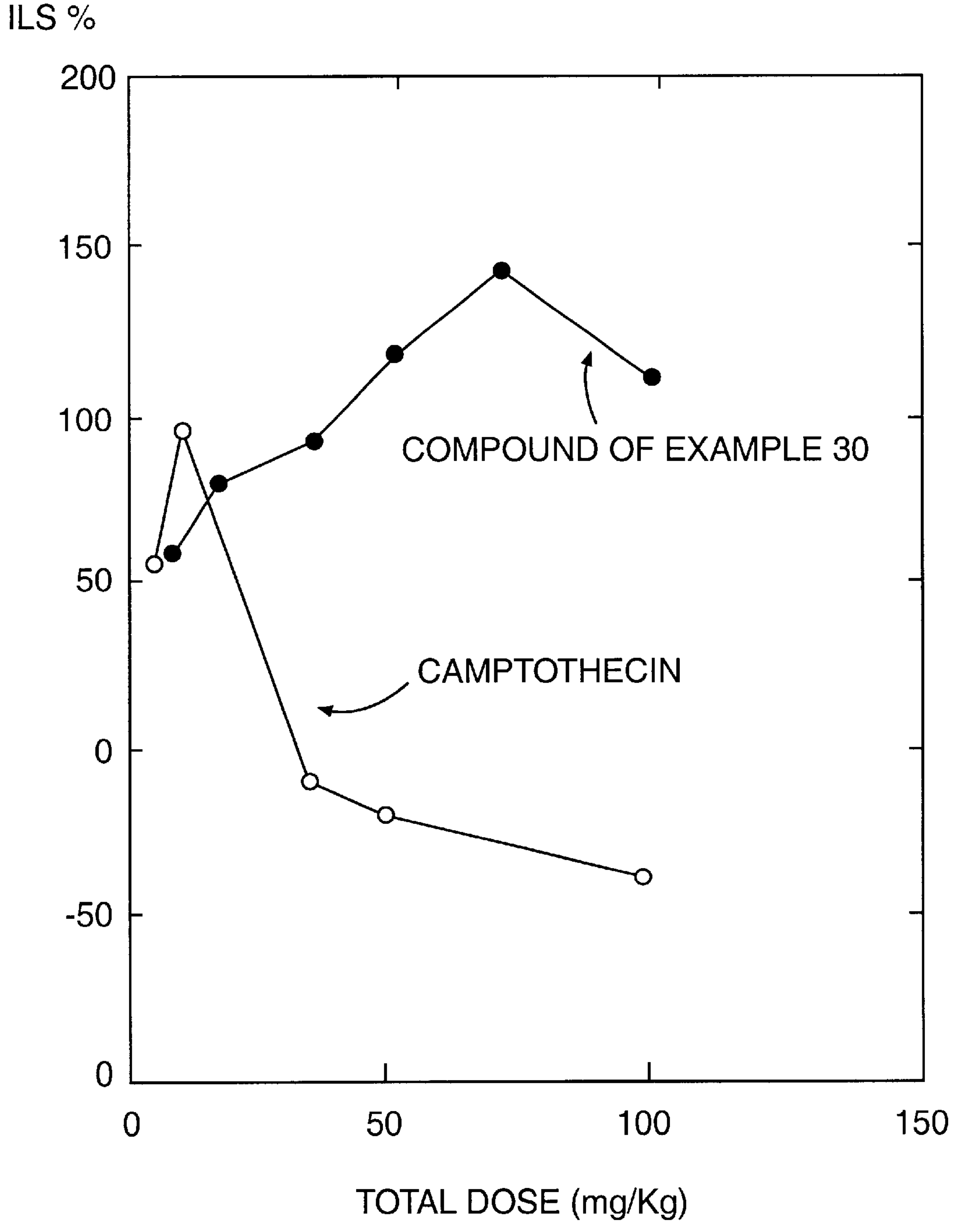
FIG. 1 illustrates the difference of ILS(%) in various dose between the compound prepared in example 30 and camptothecin.

This invention is explained in more detail by the following examples and experiments, but the claims are not limited to these examples and experiments.

EXAMPLES 1

Preparation of 3-morpholino-1-(2'-nitrophenyl)propan-1-one

A solution of morpholine (2.27 g, 0.026 mol) in ethanol (10 ml) was treated with c-HCl (3 ml) for 10 mins, concentrated under reduced pressure to prepare morpholine HCl salt. To this mixture, 2'-nitroacetophenone (3.3 g, 0.02 mol), paraformaldehyde (0.8 g, 0.029 mol), c-HCl (0.1 ml) and anhydrous ethanol (10 ml) were added. The reaction mixture was stirred under reflux for 30 hrs. This reaction mixture was then cooled to room temperature, alkalized with 10% sodium carbonate solution, and the reaction mixture was extracted with dichloromethane(3×50 ml). The organic layer was dried over anhydrous sodium sulfate and concentrated under reduced pressure to give the crude product. The crude product was purified by flash column chromatography with 5% ethanol in dichloromethane to give the desired product (1.5 g, 35%) as an oil.

$^1H$-NMR ($CDCl_3$) δ 3.1 (m, 3H), 3.5 (m, 4H), 3.75 (m, 3H), 3.99 (m, 2H), 7.85 (m, 3H), 8.15 (d, 1H, J=8 Hz)

EXAMPLE 2

Preparation of 3-piperidino-1-(2'-nitrophenyl) propan-1-one

In the same procedure as in EXAMPLE 1, the desired product (458 mg, 29%) was yielded using piperidine (515 mg, 6.06 mmol), 2'-nitroacetophenone (1 g, 6.06 mmol), paraformaldehyde (260 mg, 8.67 mmol); c-HCl (1 ml) and anhydrous ethanol.

$^1H$-NMR ($CDCl_3$) δ 1.5 (m, 6H), 2.38 (t, 4H, J=5 Hz), 2.76 (t, 2H, J=6 Hz), 3.00 (t, 2H, J=6 Hz), 3.99 (m, 2H), 7.40–7.75 (m, 3H), 8.13 (d, 1H, J=8 Hz)

EXAMPLE 3

Preparation of 3-pyrrolidino-1-(2'-nitrophenyl) propane-1-one

In the same procedure as in EXAMPLE 1, the desired product (347 mg, 23%) was yielded using pyrrolidine (560 mg, 7.88 mmol), 2'-nitroacetophenone (1 g, 6.06 mmol), paraformaldehyde (260 mg, 8.67 mmol), c-HCl (1 ml) and anhydrous ethanol (5 ml).

EXAMPLE 4

Preparation of 3-(N-benzyl-N-carbobenzyloxyamino)-1-(2'-nitrophenyl)propane-1-one A solution of benzylamine (2.79 g, 0.026 mol) in ethanol (10 ml) was treated with c-HCl (3 ml) for 10 min, concentrated under reduced pressure to prepare benzylamine·HCl salt.

To this solution, 2'-nitroacetophenone (3.3 g, 0.02 mol), paraformaldehyde (800 mg, 0.029 mol), c-HCl (0.1 ml) and anhydrous ethanol (10 ml) were added.

The reaction mixture was stirred under reflux for 30 hrs. This reaction mixture was then cooled to room temperature, alkalized with 10% sodium carbonate solution, and the reaction mixture was extracted with dichloromethane (3×50 ml) The organic layer was dried over anhydrous magnesium sulfate and concentrated under reduced pressure to give the crude product, which was dissolved in dichloromethane and cooled to 0° C. To this mixture, triethylamine (1.2 g, 0.012 mol) was added and followed by another dropwise addition of benzylchloroformate (2 ml). The reaction mixture was stirred under nitrogen flow at 0° C. for 1 hr, heated to room temperature and then stirred for additional 5 hrs.

After removing the solvent under reduced pressure, the mixture was dissolved in ethylacetate (100 ml). The organic layer was washed with water (3×30 ml) and brine (30 ml) and dried over anhydrous sodium sulfate. After the filtration, the crude product was obtained by removing the solvent. The residue was purified by flash column chromatography with n-hexane-ethylacetate(1:10) to give the desired product (1.5 g, 36%).

$^1H$-NMR ($CDCl_3$) δ 3.0 (m, 2H), 3.70 (t, 2H, J=7 Hz), 4.60 (s, 2H), 5.17 (s, 2H), 7.10–7.70 (m, 13H), 8.10 (d, 1H, J=8 Hz)

In the same procedure as in EXAMPLE 4, the compounds of EXAMPLE 5–8 were prepared and the results were as follows:

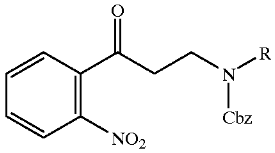

| EXAMPLE | R | $^1H$-NMR:δ |
|---|---|---|
| 5 | $CH_2CH_3$ | 8.102(d, 1H, J=1.2Hz), 7.596–7.315(m, 8H), 5.125(s, 2H), 3.762–3.61(m, 4H), 1.853(t, 2H, J=6.4Hz), 1.159(t, 3H, J=7.2Hz) |
| 6 | $CH_2CH_2CH_3$ | 8.124(d, 1H, J=1.2Hz), 7.700–7.272(m, 8H), 5.125(s, 2H), 3.717(t, 2H, J=3.6Hz), 3.322–3.279(m, 2H), 1.624–1.546(m, 4H) 0.894(t, 3H) |
| 7 | $CH(CH_3)_2$ | 8.115(d, 1H), 7.613–7.261(m, 8H) 5.135(s, 2H), 4.488–4.210(m, 1H) 3.639(t, 2H, J=7.2Hz), 1.260(t, 2H, J=7.2Hz), 1.165(d, 6H, J=6.4Hz) |
| 8 | $CH_2CH_2OH$ | 8.119(d, 1H, J=8.0Hz), 7.623–7.261(m, 8H), 5.127(s, 2H), 3.802–3.719(m, 2H), 3.557(t, 2H, J=5.2Hz), 3.392–3.353(m, 2H), 3.068–3.051(m, 2H) |

EXAMPLE 9

Preparation of 3-(N-2'-acetoxyethyl-N-carbobenzyloxyamino)-1-(2'-nitrophenyl)propane-1-one A mixture of 3-[(N-(2'-hydoxyethyl)-N-carbobenzyloxyamino )]-1-(2'-nitrophenyl)propane -1-one (40 mg, 0.107 mmol) and 4-dimethylamino pyridine (1.2 mg, 0.01 mmol) was dissolved in anhydrous dichloromethane(2 ml), then added triethylamine (0.02 ml, 0.160 mmol) and acetic anhydride(0.02 ml, 0.214 mmol). The reaction mixture was stirred at room temperature for 30 mins and washed with a saturated ammonium chloride aqueous solution, water and brine successively. Then, the organic layer was dried over anhydrous magnesium sulfate and concentrated under reduced pressure. The residue, so obtained, was purified by column chromatography with ethylacetate-n-hexane (1:3) to give the desired product (40 mg, 90%) as a yellow oil.

$^1H$-NMR (400 MHz, $CDCl_3$) δ 8.123 (d, 1H, J=8.4 Hz), 7.607–7.261 (m, 8H), 5.136 (s, 2H), 4.194 (m, H), 3.784–3.754 (m, 2H), 3.660–3.646 (m, 2H), 3.172 (m; 2H), 2.047 (s, 3H)

EXAMPLE 10

Preparation of 3-morpholino-1-(2'-aminophenyl)propane-1-one

To a solution of 3-morpholino-1-(2'-nitrophenyl) propane-1-one(200 mg, 0.758 mmol) dissolved in 10 ml of 95% ethanol was added sodium dithionite(660 mg, 3.79 mmol) and the reaction mixture was stirred under reflux for 3 hrs. The reaction mixture was concentrated under reduced pressure. The residue was purified by flash column chromatography with ethanol-dichloromethane-triethylamine to yield the desired product (174 mg, 89%) as an oil.

$^1H$-NMR ($CDCl_3$) δ 3.20 (m, 3H), 3.50 (m, 3H), 3.5 (m, 4H), 3.99 (m, 2H), 7.5–7.8 (m, 3H), 8.08 (d, 1H, J=8 Hz)

EXAMPLE 11

Preparation of 3-piperidino-1-(2'-aminophenyl) propane-1-one

The same procedure as in EXAMPLE 10 was applied to the compound of EXAMPLE 2 (200 mg, 0.758 mmol) and sodium dithionite(660 mg, 3.79 mmol) so that the desired product (174 mg, 89%) was yielded.

EXAMPLE 12 Preparation of 3-pyrrolidino-1-(2'-aminophenyl)propane-1-one

The same procedure as in EXAMPLE 10 was applied to the compound of EXAMPLE 3 (400 mg) and sodium dithionite (1.052 g, 6.05 mmol) so that the desired product (235 mg) was yielded.

In the same procedure as used in EXAMPLE 10, the compounds of EXAMPLE 13–17 were prepared and the results were as follows:

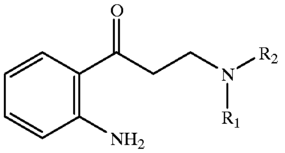

| EXAMPLE | $R_2$ | $R_1$ | $^1H$-NMR:δ |
|---|---|---|---|
| 13 | $CH_2CH_3$ | Cbz | 7.365–7.262(m, 9H), 5.144(s, 2H), 3.764–3.71(m, 4H), 1.871–1.838(m, 2H), 1,253(t, 3H, J=7.2Hz) |
| 14 | $CH_2CH_2CH_3$ | Cbz | 7.885–7.230(m, 9H), 5.142(s, 2H), 3.668–3.613(m, 2H), 3.265(t, 2H, J=6.4Hz), 1.616–1.513(m, 4H), 0.895(t, 3H) |
| 15 | $CH(CH_3)_2$ | Cbz | 7.496(d, 1H, J=7.28Hz), 7.377–7.349(m, 3H), 7.299–2.227(m, 5H) 5.172(s, 2H), 4.376–4.216(m, 1H), 3.534–3.371(m, 4H), 1.240–1.044(m, 6H) |
| 16 | $CH_2Ph$ | Cbz | 3.17(m, 2H), 3.65(m, 2H), 4.55(s, 2H), 5.10(s, 2H), 6.20(brs, $NH_2$), |

-continued

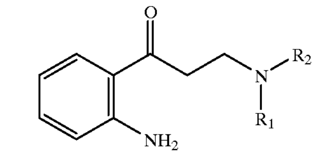

| EXAMPLE | $R_2$ | $R_1$ | $^1$H-NMR:δ |
|---|---|---|---|
| 17 | $CH_2CH_2OAc$ | Cbz | 7.10–7.70(m, 13H), 8.10(d, 1H, J=8Hz) 7.771(d, 1H, J=7.6Hz), 7.574–7.262(m, 8H), 6.641(d, 2H, J=7.6 Hz), 5.114(s, 2H), 4.186(m, 2H) 3.773–3.169(m, 6H), 2.042(s, 3H) |

EXAMPLE 18

Preparation of dl-7-[2-(N-benzyl-N-carbobenzyloxyamino) ethyl]camptothecin

A mixture of 3-(N-benzyl-N-carbobenzyloxyamino) -1-(2'-aminophenyl)propane-1-one(543 mg, 1.4 mmol) and 4-ethyl-6-oxo-1,4,7,8-tetrahydro-4-hydroxy-pyrano [3,4-f] indolizine-3,10(6H)-dione (263 mg, 1.0 mmol) was dissolved in toluene (50 ml). The reaction mixture was stirred under reflux for 30 mins, and ρ-toluenesulfonic acid (25 mg, 0.13 mmol) was added to the mixture. The reaction mixture was stirred in a Dean-Stark trap under reflux for 9 hrs. The solvent was removed under reduced pressure and the residue was purified by flash column chromatography with ethylacetate-dichloromethane (1:1) to give the desired product (507 mg, 59%) as a yellow powder.

$^1$H-NMR ($CDCl_3$) δ 1.04 (t, 3H, J=8 Hz), 1.90 (m, 2H), 3.10–3.90 (m, 4H), 4.53 (s, ½x2H), 4.61 (s, ½x2H), 4.95 (s, ½x2H), 5.07 (s, ½x2H), 5.30 (s, 2H), 5.31 (d, 1H, J=16 Hz), 5.75 (d, 1H, J=16 Hz), 7.20–8.20 (m, 15H)

In the same procedure as in EXAMPLE 18, the compounds of EXAMPLE 19 to 24 were prepared and the results were as follows:

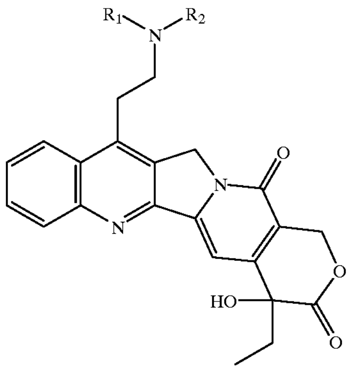

| EXAMPLE | $R_2$ | $R_1$ | $^1$H-NMR($CDCl_3$)δ |
|---|---|---|---|
| 19 | $CH_2CH_2CH_3$ | Cbz | 8.236–7.261(m, 10H), 5.757, 5.324 (ABq, 2H, J=16Hz), 5.293(s, 2H), 5.193(s, 2H), 3.593–3.199(m, 4H) 1.942–1.863(m, 2H), 1.634–1.516 (m, 4H), 1.047(t, 3H, J=7.2Hz), |

-continued

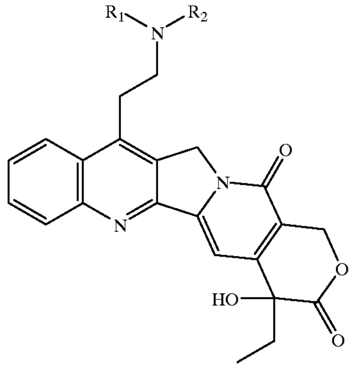

| EXAMPLE | $R_2$ | $R_1$ | $^1$H-NMR($CDCl_3$)δ |
|---|---|---|---|
| | | | 0.944–0.842(m, 3H) |
| 20 | $CH(CH_3)_2$ | Cbz | 8.197(d, 1H), 7.926–7.628(m, 3H) 7.485–7.365(m, 6H), 5.694(d, 1H, J=13.08Hz), 5.552–5.270(m, 3H) 5.246(s, 2H), 4.476–4.310(m, 1H), 3.514–3.456(m, 4H), 1.997–1.910 (m, 2H), 1.248–1,208(m, 6H), 1.044(t, 3H, J=5.92Hz) |
| 21 | $CH_2CH_2OAc$ | Cbz | 8.344–7.261(m, 10H), 5.748(d, 1H J=16.8Hz), 5.308(d, 1H, J=16.8Hz) 5.298(s, 2H), 5.113(s, 2H), 4.255–4.126(m, 2H), 3.791–3.371 (m, 6H), 2.041(s, 3H), 1.954–1.610(m, 2H), 1.042(t, 3H, J=7.2Hz) |

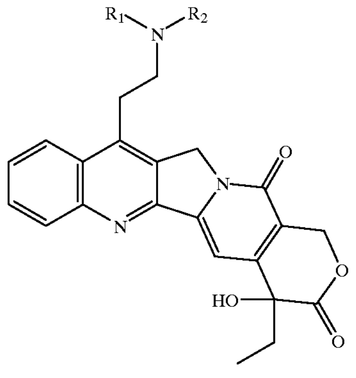

| EXAMPLE | $R_1$ $R_2$ | $^1$H-NMR(CDCl)δ |
|---|---|---|
| 22 | piperidino | $^1$H-NMR(200MHz, DMSO-$d_6$) 0.92(t, J=6Hz, 3H), 1.32(m, 6H), 1.90(m, 2H), 2.34(s, 3H), 2.90(m, 2H), 3.30 (m, 6H), 5.48(s, 2H), 5.49(s, 2H), 6.58(s, 1H), 7.16(d, J=8Hz, 2H), 7.52(d, J=8Hz, 2H), 7.77–8.30(m, 4H) |
| 23 | pyrrolidino | $^1$H-NMR(200MHz, DMSO-d6)0.94(t, J=6Hz, 3H), 1.25(m, 4H), 1.87(m, 2H), 2.33(s, 3H), 2.90(m, 2H), 3.11(m, 6H), 3.53(s, 1H), 5.52(s, 2H), 5.53(s, 2H), 6.60(s, 1H), 7.15(d, J=8Hz, 2H), 7.51(d, J=8Hz, 2H), 7.77–8.30(m, 4H) |
| 24 | morpholino | $^1$H-NMR(200MHz, $CDCl_3$)δ0.86(t, J=6Hz, 3H), 1.89(m, 2H), 2.25(s, 3H) 2.85(m, 2H), 3.05(m, 2H), 3.51(m, 4H), 3.71(m, 4H), 5.39(s, 2H), 5.40 |

-continued

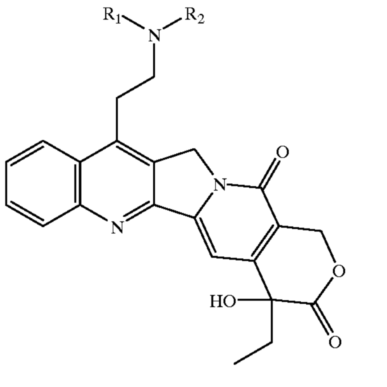

| EXAMPLE | $R_1$ | $R_2$ | $^1$H-NMR(CDCl)δ |
|---|---|---|---|
| | | | (s, 2H), 6.49(s, 1H), 7.08(d, J=8Hz, 2H), 7.44(d, J=8Hz, 2H), 7.70–8.30(m, 4H) |

EXAMPLE 25

Preparation of dl-7-[2-(N-hydroxyethyl-N-carbobenzyloxyamino)ethyl]camptothecin

A mixture of dl-7-[2-(N-acetoxyethyl-N-carbobenzyloxyamino)ethyl]camptothecin (28.2 mg, 0.05 mmol) and potassium carbonate (25 mg, 0.15 mmol) was dissolved in mixed a solution of methanol and water (1:1, 1.5 ml) and the reaction mixture solution was stirred at room temperature for 3 hrs. The reaction mixture was acidified with 1N HCl solution, extracted with dichloromethane and washed with brine. The organic layer was dried over anhydrous sodium sulfate, filtered and concentrated under reduced pressure. The residue was purified by flash column chromatography with dichloromethane-methanol (20:1) to give the desired product (17 mg, 60%) as a yellow solid.

$^1$H-NMR (400 MHz, $CDCl_3$) δ 8.171–7.762 (m, 10H), 5.710 (d, 2H, J=16.8 Hz), 5.308 (d, 2H, J=16.8 Hz), 5.301 (s, 2H), 5.207 (s, 2H), 3.868–3.466 (m, 8H), 1.926–1.832 (m, 2H), 1.033 (t, 3H, J=7.6 Hz)

EXAMPLE 26

Preparation of dl-7-[2-(N-benzylamino) ethyl] camptothecin dl-7-[2-(N-Benzyl-N-carbobenzyloxyamino)ethyl] camptothecin (50 mg, 0.08 mmol) was dissolved in glacial acetic acid (20 ml) and treated with 10% Pd/C (25 mg). The reaction mixture was stirred under hydrogen flow of 40 psi for 9 hrs, and the catalyst was removed through cellite pad by filtration under reduced pressure. The filtrate was concentrated under reduced pressure. The residue was purified by flash column chromatography with 10% methanol-dichloromethane to give the desired product (24 mg, 63%) as a yellow powder.

$^1$H-NMR (400 MHz, $CDCl_3$) δ 0.89 (t, 3H, J=8 Hz), 1.87 (m, 2H), 2.90 (m, 2H), 3.5 (m, 4H), 3.73 (s, 1H), 5.33 (s, 2H), 5.43 (s, 2H), 6.52 (s, 1H), 7.25 (m, 6H), 7.70–8.30 (m, 4H)

EXAMPLE 27

Preparation of dl-7-[2-(N-acetoxyethylamino) ethyl] camptothecin

The same procedure as in EXAMPLE 26, was carried out.

$^1$H-NMR (400 MHz, $CDCl_3$+MeOH-$d_4$) δ 8.323 (d, 1H, J=8.8 Hz), 8.138 (d, 1H, J=8.4 Hz), 7.812 (t, 1H, J=6.8 Hz), 7.675 (t, 1H, J=6.8 Hz), 7.647 (s, 1H), 5.742 (d, 1H J=16.4 Hz), 5.324–5.284 (m, 2H), 4.169–4.122 (m, 2H), 3.373 (t, 2H, J=7.6 Hz), 3.108–3.040 (m, 4H), 2.090 (s, 3H), 2.024 (s, 3H), 1.955–1.803 (m, 2H), 1.033 (t, 3H, J=7.6 Hz)

EXAMPLE 28

Preparation of dl-7-[2-(N-hydroxyethyl amino)ethyl] camptothecin

The same procedure as in EXAMPLE 26, was carried out.

$^1$H-NMR ($CDCl_3$+MeOH-$d_4$) 8.284 (d, 1H, J=8.0 Hz), 8.226 (d, 1H, J=8.8 Hz), 7.863 (t, 1H, J=6.8 Hz), 7.756 (t, 1H, J=6.8 Hz), 7.730 (s, 1H), 5.682 (d, 1H,J=13.6 Hz), 5.641 (d, 1H, J=13.6 Hz), 5.130 (s, 2H), 3.800–3.190 (m, 8H), 1.962–1.898 (m, 2H), 1.031 (t, 3H, J=4.4 Hz), 2.035 (s, 3H)

EXAMPLE 29

Preparation of dl-7-[2-(N-ethylamino)ethyl]camptothecin

A mixture of 2'-amino-2-(N-carbobenzyloxy-N-ethylamino)propiophenone (34 mg, 0.11 mmol) and 4-ethyl-6-oxo-1,4,7,8-tetrahydro-4-hydroxy-pyrano[3, 4-f] indolizine-3,10(6H)-dione(34 mg, 0.1 mmol) was dissolved in toluene and was refluxed for 30 mins. After addition of ρ-toluenesulfonic acid (19.2 mg, 0.11 mmol), the reaction mixture was then refluxed in a Dean-Stark trap for 3 hrs. The reaction mixture was concentrated under reduced pressure, and the residue was purified by column chromatography with dichloromethane-methanol (10:1) to give the desired product(40 mg, 67%) as a solid.

$^1$H-NMR (400 MHz, DMSO-$d_6$) δ 8.280 (d, 1H, J=8.6 Hz), 8.184 (d, 1H, J=7.4 Hz), 7.873–7.753 (m, 2H), 7.471 (d, 2H, J=7.2 Hz), 7.111 (d, 2H, J=7.2 Hz), 7.356 (s, 1H), 6.523 (s, 1H), 5.439 (s, 2H), 3.534–2.753 (m, 6H), 2.217 (s, 3H), 1.671–1.643 (m, 2H), 1.230 (t, 3H, J=6.8 Hz), 0.743 (t, 3H,J=7.2 Hz)

EXAMPLE 30

Preparation of dl-7-[2-(N-isopropylamino)ethyl] camptothecin

The same procedure as in EXAMPLE 29 was carried out.

$^1$H-NMR (400 MHz, DMSO-$d_6$) δ 8.870–8.567 (m, 2H), 8.298–8.155 (m, 2H), 7.867 (d, 2H, J=7.6 Hz), 7.741 (s, 1H), 7.500 (d, 2H, J=7.6 Hz), 5.828 (s, 2H), 5.795 (s, 2H), 3.958–3.820 (m, 2H), 2.666 (s, 3H), 2.320–2.200 (in, 2H), 1.614 (d, 6H, J=6.4 Hz), 1.533 (t, 2H), 1.267 (t, 3H)

EXAMPLE 31 dl-7-[2-(Morpholino)ethyl]camptothecin trifluoro-acetate

The same procedure as in EXAMPLE 24 was carried out except that trifluoroacetic acid was used instead of p-toluenesulfonic acid.

$^1$H-NMR (200 MHz, DMSO-$d_6$) δ 0.92 (t, J=6 Hz, 3H), 1.94 (m, 2H), 2.90 (m, 4H), 3.30–3.65 (m, 8H), 5.47 (s, 2H), 5.48 (s, 2H), 6.56 (s, 1H), 7.70–8.30 (m, 4H)

EXAMPLE 32

Preparation of 6-cyano-1,1-(ethylenedioxy) -7-[1'-(ethoxycarbonyl)-3'-(methoxymethyloxypropyl]-5-oxo-$\Delta^{6}$(8)-tetrahydroindolizine 6-Cyano-1,1-(ethylenedioxy)-7-[(ethoxycarbonyl) methyl]-5-oxo-$\Delta^{6(8)}$-tetrahydroindolizine (608.6 mg, 2 mmol) was dissolved in anhydrous dimethylformamide (3 ml), cooled to 5° C. and after addition of potassium t-butoxide (258.1 mg, 2.3 mmol), the reaction mixture was stirred at the same temperature for 30 mins. To this mixture, 2-brmoethanolmethoxy-methylether (1.352 g, 8 mmol) was added and the reaction mixture was stirred at 45–50° C. for 20 hrs. The reaction mixture was diluted with water(50 ml), extracted with dichloromethane (100 ml). The organic layer was washed with water(80 ml) and brine(80 ml), dried over anhydrous magnesium sulfate and concentrated under reduced pressure. The residue was purified by column chromatography with ethylacetate-n-hexane (2:1) to give the desired product (734.8 mg, 95%) as a pale yellow solid.

IR(neat) 2224, 1734, 1656 $cm^{-1}$ $^1$H-NMR (400 MHz, $CDCl_3$) δ 1.254 (t, 3H, J=6.8 Hz), 1.987–2.020 (m, 1H), 2.410 (t, 2H, J=6.8 Hz), 2.43–2.449 (m, 1H), 3.447–3.485 (m, 1H) 3.564–3.603 (m, 1H), 4.117–4.201 (m, 7H), 4.225 (q, 2H J=7.6 Hz),4.584, 4.609 (ABq, 2H, J=6.8 Hz),6.367 (s, 1H)

MS(EI) m/e 392 ($M^+$), 377 ($M^+$–$CH_3$), 361 ($M^+$–$OCH_3$), 347 ($M^+$–$C_2H_5O$)

EXAMPLE 33

Preparation of 6-(acetamidomethyl)-1,1-(ethylenedioxy)-7-[1'-(ethoxycarbonyl)-3° C.-(methoxymethyl oxypropyl)]-5-oxo-$\Delta^{6(8)}$-tetrahydroindolizine 250 Drops of Raney-Nickel (50% aqueous slurry) was washed with water (5 ml) and acetic acid (10 ml) 5 times respectively and added into a parr bottle.

To this solution, a compound(743.8 mg, 1.9 mmol), obtained in EXAMPLE 32, acetic anhydride(30 ml) and acetic acid (10 ml) were added and the reaction mixture was hydrogenated at a pressure of 45 psi and 45–50° C. for 3 hrs. The catalyst was removed by filtration and the filtrate was concentrated under reduced pressure. The residue was purified by column chromatography with dichloromethane-methanol (20:1) to give the desired product(789.5 mg, 95%) as a yellow oil.

IR(neat) 1733, 1660, 1635 $cm^{-1}$ $^1$H-NMR (400 MHz, $CDCl_3$) δ 1.214 (t, 3H, J=6.8 Hz), 1.924 (s, 3H), 1.939–1.98 (m, 1H), 2.382 (t, 2H, J=6.8 Hz), 2.399–2.40 (m, 1H), 3.343 (s, 3H), 3.44–3.58 (m, 2H), 4.075–4.131 (m, 7H), 4.145 (q, 2H), 4.34, 4.39 (d, d, 2H), 4.571, 4.592 (ABq, 2H, J=6.8 Hz), 6.306 (s, 1H), 6.61 (brs, 1H)

MS(EI) m/e 438 (M+), 423 ($M^+$–$CH_3$), 407 ($M^+$–$OCH_3$), 395 ($M^+$–$COCH_3$), 393 (M'—$C_2H_5O$)

EXAMPLE 34

Preparation of 6-(acetoxymethyl)-1,1-(ethylenedioxy)-7-[1'-(ethoxycarbonyl)-3'-(methoxymethyloxypropyl)]-5-oxo-$\Delta^{6}$(8)-tetrahydroindolizine To a compound (789.5 mg, 1.8 mmol) obtained in EXAMPLE 33, acetic anhydride(15 ml), acetic acid(5 ml) and sodium nitrite(621.2 mg, 9 mmol) were added and the reaction mixture was stirred at 5 to 10° C. for 6 hrs. After removing the inorganic material, so formed by filtration, the filtrate was concentrated under reduced pressure to give nitroso compound. With addition of carbon tetrachlonride (50 ml), the mixture was heated under reflux for 18 hrs. The reaction mixture was washed with water (10 ml) and brine (10 ml), dried over anhydrous magnesium sulfate and concentrated under reduced pressure. The residue was purified by column chromatography. with dichloromethane -methanol(20:1) to give the desired product (720 mg, 91%) as a colorless oil.

IR(neat) 1740, 1733, 1654 $cm^{-1}$ $^1$H-NMR (400MHZ, $CDCl_3$) δ 1.217 (t, 3H, J=6.8 Hz), 1.86–1.95 (m, 1H), 2.056 (s, 3H), 2.368 (t, 2H), 2.38–2.43 (m, 1H), 3.333 (s, 3H), 3.41–3.57 (m, 2H), 4.087–4.119 (m, 9H), 4.569 (s, 2H), 5.259 (s, 2H), 6.304 (s, 1H)

MS(EI) m/e 439 ($M^+$), 408 ($M^+$–$OCH_3$), 396 ($M^+$–$COCH_3$)

EXAMPLE 35

Preparation of 1,1-(ethylenedioxy)-(5'-methoxymethyloxyethyl-2'H,5'H,6'H-6-oxopyrano) [3',4'-f]-5-oxo-$\Delta^{6(8)}$-tetrahydroindolizine A mixture of the compound (720 mg, 1.64 mmol) obtained in prepared by EXAMPLE 34 and methanol (15 ml) was added to $LiOH.H_2O$ (172 mg, 4.1 mmol) dissolved in water (5 ml) and stirred at 25 to 30° C. for 2 hrs. The reaction mixture was concentrated under reduced pressure to remove methanol and with addition of water(15 ml), dichloromethane(50 ml) and acetic acid (5 ml), the reaction mixture was stirred at 25 to 30° C. for 10 hrs. The organic layer was separated from the reaction mixture, washed with water (10 ml) and brine (10 ml) and dried over anhydrous magnesium sulfate. The organic layer was concentrated under reduced pressure. The residue was purified by column chromatography with dichloromethanemethanol (30:1) to give the desired product (720 mg, 91%) as a white solid.

IR(neat) 1747, 1662 $cm^{-1}$ $_1$H-NMR (400 MHz, $CDCl_3$) δ 2.178–2.216 (m, 2H), 2.404 (t, 2H, J=6.8 Hz), 3.371 (s, 3H), 3.599–3.643 (m, 2H), 3.701 (t, 1H, J=6.8 Hz), 4.109–4.192 (m, 6H), 4.618 (s, 2H), 5.278, 5.43 (ABq, 2H, J=16.4 Hz), 6.169 (s, 1H)

MS(EI) m/e 351 ($M^+$), 320 ($M^+$–$OCH_3$), 307 ($M^+$–$CO_2$)

EXAMPLE 36

Preparation of 1,1-(ethylenedioxy)-(5'-methoxymethyloxyethyl-5'-hydroxy-2'H,5'H,6'H-6-oxopyrano)[3',4'-f]-5-oxo-$\Delta^{6(8)}$-tetrahydroindolizine Potassium t-butoxide (273 mg, 2.43 mmol) was added to a mixture of the compound (570.3 mg, 1.63 mmol) obtained in EXAMPLE 35 dissolved in anhydrous DMF (20 ml) and stirred at 0 to 5° C. for 30 mins. The reaction mixture was cooled to −10 to −5° C. and with addition of triethyl phosphite (974 μl, 5.68 mmol), the mixture was stirred for 2.5 hrs, while bubbling the oxygen. Water (10 ml) was added to the mixture and pH was adjusted to 3.5 with 1N-HCl. Then, the reaction mixture was extracted with dichloromethane (30 ml×2 times), washed with water (20 ml), and brine (20 ml) and dried over anhydrous magnesium sulfate. The organic layer was concentrated under reduced pressure. The residue was purified by column chromatography with dichloromethane-methanol (25:1) to give the desired product (416.4 mg, 69.8%) as a white solid.

IR(neat) 3503, 1749, 1654 $cm^{-1}$ $^1$H-NMR (400 MHz, $CDCl_3$) δ 1.919–1.974 (m, 1H), 2.010–2.063 (m, 1H), 2.348 (t, 2H, J=6.8 Hz), 3.30 (s, 3H), 3.542–3.597 (m, 1H), 3.639–3.684 (m, 1H), 4.002–4.1541 (m, 7H), 4.516, 4.494 (ABq, 2H, J=6.4 Hz), 5.111, 5.557 (ABq, 2H, J=16 Hz), 6.541 (s, 1H)

MS(EI) m/e 367 ($M^+$), 336 ($M^+$–$OCH_3$), 323 ($M^+$–$CO_2$)

EXAMPLE 37 :

Preparation of 1,5-dioxo-(5'-hydroxyethyl-5'-hydroxy-2'H, 5'H,6/H-6-oxopyrano)[3',4'-f]-$\Delta^{6(8)}$-tetrahydroindolizine A mixture of THF (200 ml), water (1 ml) and 6N HCl (2.5 ml) was added to the compound (146.1 mg, 0.4 mmol) obtained in EXAMPLE 36 and stirred at 50–55° C. for 1 hr. The reaction mixture was concentrated under reduced pressure. The residue was purified by Dianion$^R$ HP-20 (Mitsubishi) with acetonitrile-water (4:1) and concentrated under reduced pressure to give the desired product (93.2 mg, 84%) as a black resin.

IR(KBr) 3470, 1749, 1654 $cm^{-1}$ $^1$H-NMR (400 MHz, $CDCl_3$) δ 1.92–2.11 (m, 2H), 2.962 (t, 2H, J=6.0 Hz), 3.674–3.86 (m, 2H), 4.326 (t, 2H, J=6.0 Hz), 5.259, 5.627 (ABq, 2H, J=16.8 Hz), 5.287 (s, 1H), 7.284 (s, 1H)

MS(EI) m/e 279 ($M^+$), 261 ($M^+$–$H_2O$), 235 ($M^+$–$C_2H_5OH$)

EXAMPLE 38

Preparation of dl-18-hydroxycamptothecin

A solution of 2-aminobenzaldehyde ethyleneacetal (75.6 mg, 0.46 mmol) and toluene (8 ml) was added to the compound (85.2 mg, 0.31 mmol) obtained in EXAMPLE 37 and refluxed in a Dean-Stark apparatus for 1 hr. p-toluene-sulfonic acid (catalytic amount) was added to the reaction mixture and refluxed again for 3 hrs. The solid, so formed, was filtered and purified by column chromatography with dichloromethane-methanol (15:1) to give the desired product (57.8 mg, 52%) as a pale brown solid.

IR(neat) 3400, 1743, 1658 $cm^{-1}$ $^1$H-NMR (400 MHz, $CDCl_3$:DMSO-$d_6$=3:1) δ 2.01–2.20 (m, 2H), 3.51–3.86 (m, 2H), 5.315 (s, 2H), 5.34, 5.55 (ABq, 2H), 6.418 (s, 1H), 7.557 (s, 1H), 7.676 (t, 1H), 7.83 (t, 1H), 8.03 (d, 1H), 8.18 (d, 1H), 8.570 (s, 1H)

MS(EI) m/e 364 ($M^+$), 320 ($M^+$–$CO_2$)

EXAMPLE 39

Preparation of dl-18-methoxymethyloxy camptothecin

Methoxymethyl chloride (6 μl, 0.08 mmol) and diisopropylethylamine (12 μl, 0.07 mmol) was added to a suspension of dl-18-hydroxycamptothecin (20 mg, 0.05 mmol) in dichloromethane (2 ml) and stirred at 25 to 30° C. for 48 hrs. With addition of dichloromethane (25 ml), the reaction mixture was washed with a saturated ammonium chloride (10 ml), water (10 ml), 10% hydrogen sulfate potassium (10 ml), water (10 ml) and brine (10 ml) successively. The organic layer was dried over anhydrous magnesium sulfate and concentrated under reduced pressure. The residue was purified by column chromatography with dichloromethane-methanol (30:1) and PTLC with dichloromethane-methanol (20:1) to give the desired product (5 mg, 23%) as a yellow solid.

IR (KBr) 3566, 1733, 1652 $cm^{-1}$ $^1$H-NMR (400 MHz, $CDCl_3$) δ 2.15–2.34 (m, 2H), 3.387 (s, 3H), 4.08–4.22 (m, 2H), 4.604 (d, d, 2H), 5.313 (s, 2H), 5.62, 5.78 (ABq, 2H), 6.6 (s, 1H), 7.68 (t, 1H), 7.726 (s, 1H), 7.84 (t, 1H), 7.96 (d, 1H), 8.24 (d, 1H), 8.41 (s, 1H)

MS(EI) m/e 408 ($M^+$) HRMS m/e M+Calcd; 408.1321, Obsd; 408.1336

In the same manner as in EXAMPLE 39, the compounds (R=H and n=2) of EXAMPLE 40 to 46, expressed by the general formula (I), were prepared.

| EXAMPLE | $R_3$ | $^1$H-NMR ($CDCl_3$ or $CDCl_3$ + $CD_3OD$) δ |
|---|---|---|
| 40 | $OCOCH_3$ | 1.970(s, 3H), 2.26–2.37(m, 2H), 4.126–4.216(m, 2H), 5.32(s, 2H), 5.66, 5.79 (Aq, 2H), 6.36(s, 1H), 7.65(s, 1H), 7.69(t, 1H), 7.86(t, 1H), 7.95 (d, 1H), 8.25(d, 1H), 8.41(s, 1H) |
| 41 | $OCOCH_2OCH_3$ | 8.3975(s, 1H), 8.2429(d, 1H, J=8.5Hz) 7.9401(d, 1H, J=8.3Hz), 7.8358(t, 1H), 7.6936(s, 1H), 7.6845(t, 1H), 5.7928 5.3225(ABq, 2H, J=16.2Hz), 5.3064(s, 2H), 4,2762–4.2991(m, 1H), 4.18–4.22 (m, 1H), 3.9794(d, 2H, J=2.4Hz), 3.4106(s, 3H), 2.2333–2.2444(m, 2H) |
| 42 | $OCH_2OCH_2CH_3$ | 8.4035(s, 1H), 8.2411(d, 1H, J=8.4Hz) 7.945(d, 1H, J=7.4Hz), 7.8409(t, 1H, J=7.0Hz), 7.7274(s, 1H), 7.6744(t, 1H J=7.0Hz), 5.7673, 5.3189(ABq, 2H, J=16.2Hz), 5.3132(s, 2H), 4.6547(ABq, 2H), 4.3373(s, 1H), 4.2345(q, 2H), 3.81(m, 1H), 3.7144(m, 1H), 2.22(m, 1H), 2.11(m, 1H), 1.2186(t, 3H) |
| 43 | $OCH_2OCH_2CH_2OCH_3$ | 8.4018(s, 1H), 8.2391(d, 1H, J=8.4Hz), 7.9423(d, 1H, J=7.6Hz), 7.8388(t, 1H), 7.7236(s, 1H), 7.6925(t, 1H), 5.7629, 5.3223(ABq, 2H, J=16.3Hz), 5.3111(s, 2H), 4.6934(d, d, 2H), 3.8514(m, 1H) 3.7011–3.7435(m, 2H), 3.65(m, 1H), 3.5602–3.5828(m, 2H), 3.3976(s, 3H), 2.01–2.22(m, 2H) |
| 44 | OCONHPh | 2.074–2.188(m, 1H), 2.308–2.361(m, 1H), 4.122–4.163(m, 1H), 4.279–4.303(m, 1H) 5.153, 5.263(ABq, 2H, J=19.2Hz) 5.464 (s, 2H), 6.707(t, 1H, J=7.2Hz) 7.013(t, 2H, J=8.0Hz), 7.202(d, 2H, J=8.0Hz), 7.350(s, 1H), 7.693(t, 1H J=7.2Hz), 7.842(t, 1H, J=8.4Hz), 8.086(d, 1H, J=8.4Hz), 8.122(d, 1H, J=8.0Hz), 8.611(s, 1H), 9.337(brs, 1H) |
| 45 | $OCONHCH_2CH_2$—Cl | 9.19(brs, 1H), 8.3989(s, 1H), 8.2469 (d, 1H, J=8.4Hz), 7.9399(d, 1H, J=7.9 Hz), 7.8384(t, 1H), 7.7171(s, 1H), 7.6727(t, 1H), 5.7667, 5.3430(ABq, 2H), 5.2748(q, 2H), 3.8914(m, 1H), 3.78(m, 1H), 3.5472–3.5995(m, 2H), 3.4507–3.4833(m, 2H), 2.22(m, 2H) |
| 46 | OCONH i-Pr. | 8.3909(s, 1H), 8.2033(d, 1H, J=8.7Hz) 7.9206(d, 1H, J=7.5Hz), 7.8150(t, 1H) 7.7022(s, 1H), 7.6551(t 1H), 5.7112, 5.2815(ABq, 2H, J=16.2Hz), 5.2778(s, |

-continued

| EXAMPLE | $R_3$ | $^1$H-NMR ($CDCl_3$ or $CDCl_3$ + $CD_3OD$) δ |
|---|---|---|
| | | 2H), 4.2720(m, 1H), 4.1706–4.1982(m, 1H), 3.6538(m, 1H), 2.2597(m, 2H), 1.1270(d, 6H) |

EXAMPLE 47

Preparation of 6-cyano-1,1-(ethylenedioxy)-7-[1'-(ethoxycarbonyl)-2'-hydroxyethyl]-5-oxo-$\Delta^{6(8)}$-tetrahydroindolizine A mixture of 35% formaldehyde (30 ml), dioxane (50 ml), water (20 ml) and ethanol (20 ml) was added to 6-cyano-1,1-(ethylenedioxy)-7-[(ethoxycarbonyl)methyl]-5-oxo-$\Delta^{6(8)}$-tetrahydroindolizine (500 mg, 1.64 mmol) and stirred at 25 to 30° C. for 15 hrs. With addition of dichloromethane (120 ml), the reaction mixture was washed with water(120 ml×3 times) and brine (120 ml). The separated organic layer was dried over anhydrous magnesum sulfate and concentrated under reduced pressure. The residue was purified by column chromatography with dichloromethane-methanol (25:1) to give the desired product (318 mg, 58%) as a white solid.

IR (KBr) 3310, 2224, 1735, 1647 $cm^{-1}$ $^1$H-NMR (400 MHz, $CDCl_3$) δ 1.275 (t, 3H, J=7.2 Hz), 2.407 (t, 2H, J=6.8 Hz), 4.029–4.221 (,m, 9H), 4.239 (q, 2H), 6.383 (s, 1H)

MS(EI) m/e 334 ($M^+$), 316 ($M^+$–$H_2O$), 304 ($M^+$–$CH_3OH$)

EXAMPLE 48

Preparation of 6-cyano-1,1-(ethylenedioxy)-7-[1'-(ethoxycarbonyl)-2'-(methoxyethoxymethyloxyethyl)]-5-oxo-$\Delta^{6(8)}$-tetrahydroindolizine Dichloromethane(0.7 ml) was added to the compound (51.6 mg, 0.15 mmol) obtained in EXAMPLE 47 and cooled in ice bath. Then, with a slow addition of diisopropylethylamine (30 μl, 0.17 mmol) and MEM-Cl (35 μl, 0.31 mmol), the resulting solution was stirred at 25 to 30° C. for 20 hrs. To the reaction mixture, dichloromethane (15 ml) was added and washed with a saturated sodium bicarbonate aqueous solution (10 ml×2 times), water (10 ml) and brine (10 ml). The separated organic layer was dried over anhydrous magnesium sulfate and concentrated under reduced pressure. The residue was purified by column chromatography with dichloromethane-methanol (25:1) to give the desired product (41 mg, 62%) as a white solid.

IR(neat) 2224, 1734, 1661 $cm^{-1}$ $^1$H-NMR (400 MHz, $CDCl_3$) δ 1.289 (t, 3H, J=6.8 Hz), 2.422 (t, 2H, J=6.8 Hz), 3.410 (s, 3H), 3.548–3.598 (m, 2H), 3.653–3.680 (m, 1H), 3.725–3.748 (m, 1H), 3.912 (dd, 1H, J=10 Hz, J=6.8 Hz), 4.098 (dd, 1H, J=10 Hz, J=6.8 Hz), 4.129–4.216 (m, 6H), 4.236 (q, 2H), 4.336 (t, 1H, J=6.8 Hz), 4.706, 4.742 (ABq, 2H, J=6.8 Hz), 6.441 (s, 1H)

MS(EI) m/e 423 ($M^+$+H), 422 ($M^+$), 392 ($M^+$–$OCH_3$), 378 ($M^+$–$C_2H_5O$)

EXAMPLE 49

Preparation of 6-(acetamidomethyl)-1,1-(ethylenedioxy)-7-[1'-(ethoxycarbonyl)-2'-(methoxyethoxymethyloxyethyl)]-5-oxo-$\Delta^{6(8)}$-tetrahydroindolizine With the compound(39.6 mg, 0.09 mmol) obtained in EXAMPLE 48, the reaction and work-up was carried out in the same procedure as in EXAMPLE 33 and then, the residue was purified by column chromatography with dichloromethane-methanol (20:1) to give the desired compound(42 mg, 96%) as a colorless oil.

IR(neat) 1733, 1661, 1656 $cm^{-1}$ $^1$H-NMR (400 MHz, $CDCl_3$) δ 1.247 (t, 3H, J=7.2 Hz), 1.943 (s, 3H), 2.393 (t, 2H, J=6.8 Hz), 3.405 (s, 3H), 3.546–3.569 (m, 2H), 3.660 –3.686 (m, 2H), 3.809 (dd, 1H, J=6.4 Hz, J=9.2 Hz), 4.093–4.192 (m, 7H), 4.205 (g, 2H), 4.467 (dq, 2H, J=6.4 Hz), 4.652 (t, 2H, J=6.8 Hz), 4.719, 4.750 (ABq, 2H, J=6.8 Hz), 6.349 (s, 1H), 6.658 (s, 1H)

MS(EI) m/e 468 ($M^+$), 453 ($M^+$–$CH_3$), 425 ($M^+$–$C_2H_5O$)

EXAMPLE 50

Preparation of 6-(acetoxymethyl)-1,1-(ethylenedioxy)-7-[1'-(ethoxycarbonyl)-2'-(methoxyethoxymethyloxyethyl)]-5-oxo-$\Delta^{6(8)}$-tetrahydroindolizine With the compound (359 mg, 0.76 mmol) obtained in EXAMPLE 49, the reaction and work-up was carried out in the same procedure as used in EXAMPLE 34 and then, the residue was purified by column chromatography with dichloromethane methanol (30:1) to give the desired compound(234 mg, 65%) as a colorless oil.

IR(neat) 1733, 1740, 1661 $cm^{-1}$ $^1$H-NMR (400 MHz, $CDCl_3$) δ 1.230 (t, 2H, J=7.2 Hz), 2.057 (s, 3H), 2.361 (t, 2H, J=6.8 Hz), 3.381 (s, 3H), 3.521–3.542 (m, 2H), 3.620–3.653 (m, 2H), 3.723 (dd, 1H, J=6.0 Hz, J=9.6 Hz), 4.082–4.209 (m, 8H), 4.225 (5, 2H), 4.716–4.675 (ABq, 2H, J=6.8 Hz), 5.259 (s, 2H), 6.313 (s, 1H)

MS(EI) m/e 469 ($M^+$), 426 ($M^+$–$COCH_3$)

EXAMPLE 51

Preparation of 6-(acetoxymethyl)-1,1-(ethylenedioxy)-7-[1'-(ethoxycarbonyl)vinyl]-5-oxo-$\Delta^{6(8)}$-tetrahydroindolizine A mixture of dry benzene (8 ml) and DBU (416 μl, 2.78 mmol) was added to the compound(522 mg, 1.1 mmol) obtained in EXAMPLE 50 and stirred at room temperature for 3 hrs. With addition of dichloromethane (20 ml), the reaction mixture was washed with a saturated ammonium chloride aqueous solution (15 ml×2) and water (15 ml). The separated organic layer was dried over anhydrous magnesium sulfate and concentrated under reduced pressure. The residue was purified by column chromatography with dichloromethane-methanol (30:1) to give the desired product (363 mg, 90%) as a yellowish white solid.

IR(neat) 1729, 1719, 1655 $cm^{-1}$ $^1$H-NMR (400 MHz, $CDCl_3$) δ 6.551 (s, 1H), 6.109, 5.773 (s, s, 1H×2), 5.008 (s, 2H), 4.243 (q, 2H, J=7.2 Hz), 4.104–4.161 (m, 6H), 2.398 (t, 2H, J=6.8 Hz), 2.021 (s, 3H), 1.293 (t, 3H, J=7.2 Hz)

MS(EI) m/e 363 ($M^+$), 320

EXAMPLE 52

Preparation of 6-(acetoxymethyl) -1,1-(ethylenedioxy)-7-[1'-(ethoxycarbonyl)-1'-(hydroxy)-2'-(hydroxy)ethyl]-5-oxo-$\Delta^{6(8)}$-tetrahydroindolizine Pyridine (3.9 ml) was added to the compound(285 mg, 1.79 mmol) obtained in EXAMPLE 51, injected with $OsO_4$ (240 mg, 0.94 mmol)(0.08M toluene, 11.8 ml) and stirred at room temperature for 4 hrs in the dark. After the reaction was completed, the reaction mixture was added with a solution of $NaHSO_3$ (480 mg) and water (7 ml) and stirred for 1 hr. The reaction mixture was extracted with dichloromethane (30 ml×5), and the combined organic layers were washed with brine and dried over anhydrous magnesium sulfate.

The organic layer was concentrated under reduced pressure. The residue was purified by column chromatography with dichloromethane-methanol (20:1) to give the desired product (280 mg, 90%) as a white solid.

IR(neat) 3307, 1735, 1654 $cm^{-1}$ $^1$H-NMR (400 MHz, $CDCl_3$) δ 6.455 (s, 1H), 5.303 (ABq, 2H, J=11. 7 Hz), 4.611 (s, 1H) 4.085–4.611 (m, 9H), 3.855, 3.826 (dd, 1H, J=6.8, 11.2 Hz), 2.641 (brt, 1H, J=6.8 Hz), 2.384 (t, 2H, J=6.8 Hz), 2.063 (s, 3H), 1.290 (t, 3H, J=6.8 Hz)

MS(EI) m/e 397 ($M^+$), 354

EXAMPLE 53

Preparation of 1,1-(ethylenedioxy)-(5'-hydroxy methyl-5'-hydroxy-2'H,5'H,6'H-6-oxopyrano)[3',4'-f]-5-oxo-$\Delta^{6(8)}$-tetrahydroindolizine With the compound(325 mg, 0.82 mmol) obtained in EXAMPLE 52, the reaction and work-up was carried out in the same procedure as in EXAMPLE 35 and then, the residue was purified by column chromatography with dichloromethane-methanol (20:1) to give the desired compound (211 mg, 84%) as a white solid.

IR(neat) 3421, 1750, 1654 $cm^{-1}$ $^1$H-NMR (400 MHz, $CDCl_3$) δ 6.599 (s, 1H), 5.564, 5.255 (ABq, 2H, J=16.0 Hz), 4.072–4.238 (m, 7H), 3.772, 3.733 (dd, 2H, J=11.6 Hz), 2.418 (t, 2H, J=6.8 Hz)

MS(EI) m/e 309 ($M^+$), 293, 280, 279, 265

HRMS m/e ($M^+$) Calcd: 309, 0849, Obsd: 309, 0.847

EXAMPLE 54

Preparation of 1,1-(ethylenedioxy)-(5'-acetoxymethyl-5'-hydroxy-2'H,5'H,6'H-6-oxopyrano)[3',4'-f]-5-oxo-$\Delta^{6(8)}$-tetrahydroindolizine The compound (119 mg, 0.38 mmol) obtained in EXAMPLE 53 was dissolved in anhydrous dichloromethane (10 ml) and with addition of pyridine (93 μl, 1.15 mmol) and acetic anhydride (47 μl, 0.50 mmol), the reaction mixture was stirred at room temperature for 20 hrs. The reaction mixture was diluted with dichloromethane (20 ml), washed with 10% potassium bisulfate aqueous solution (20 ml), water (20 ml) and brine (20 ml), and dried over anhydrous magnesium sulfate.

The organic layer was concentrated under reduced pressure. The residue was purified by column chromatography with dichloromethane-methane (20:1) to give the desired compound (127 mg, 94%) as a white solid.

IR(neat) 3437, 1751, 1657 $cm^{-1}$ $^1$H-NMR (400 MHz, $CDCl_3$) δ 6.586 (s, 1H), 5.636, 5.295 (ABq, 2H, J=16.4 Hz), 4.302 (d, 1H, J=11.2 Hz), 4.116–4.215 (m, 7H), 4.004 (s, 1H), 2.427 (t, 2H, J=6.8 Hz), 2.084 (s, 3H)

In the same procedure as used in EXAMPLE 54, the compounds of EXAMPLE 55 to 57 were prepared and the results were as follows:

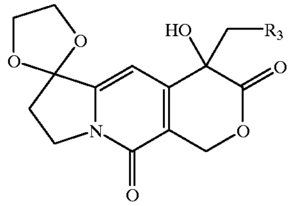

| EXAMPLE | $R_3$ | $^1$H-NMR($CDCl_3$)δ |
|---|---|---|
| 55 | OCONHPh | 8.205(brs, 1H), 7.260–7.436(m, 4H), 7.055(d, 1H), 6.661(s, 1H), 5.587, 5.357(ABq, 2H), 4.366, 4.319(d, d, 2H, J=11.2Hz), 4.101–4.227(m, 6H), 2.413(t, 2H, J=6.8Hz) |
| 56 | OCONH i-Pr. | 6.61(s, 1H), 5.64, 5.56(ABq, 2H), 4.66(d, 1H), 4.53(d, 1H), 4.1253(m, 6H), 3.7981–3.8826(m, 1H), 2.4203(t, 2H), 1.1478(d, 6H) |
| 57 | $O\underset{\underset{O}{\|}}{C}CH_2OCH_3$ | 6.5831(s, 1H), 5.6356, 5.3385(ABq, 2H, J=16.4Hz), 4.3821(d, 1H, J=11.4 Hz), 4.2693(d, 1H, J=11.4Hz), 4.1275–4.2176(m, 6H), 4.0542(d, 2H, J=2.0Hz), 3.4240(s, 3H), 2.4235(t, 2H, J=6.8Hz) |

EXAMPLE 58

Preparation of 1,5-dioxo-(5'-acetoxymethyl-5'-hydroxy-2'H, 5'H,6'H-6-oxopyrano)[3',4'-f]-$\Delta^{6(8)}$-tetrahydroindolizine 80% trifluoroacetic acid(1.3 ml) was added to the compound (127 mg, 0.36 mmol) obtained in EXAMPLE 54 and stirred at room temperature for 2 hrs. The reaction mixture was concentrated under reduced pressure and with addition of brine, the reaction mixture was extracted with dichloromethane (20 ml×3) and dried over anhydrous magnesium sulfate. The organic layer was concentrated under reduced pressure. The residue was purified by column chromatography with dichloromethane-methanol (20:1) to give desired product (theoretical yield) as a yellow solid.

IR (KBr) 3412, 1746, 1660 $cm^{-1}$ $^1$H-NMR (400 MHz, $CDCl_3$) δ 7.318 (s, 1H), 5.687, 5.388 (ABq, 2H, J=17.1 Hz), 4.405 (t, 2H), 4.370 (d, 1H, J=11.7 Hz), 4.155 (d, 1H, J=11.7 Hz), 3.007 (t, 2H, J=6.8 Hz), 2.080 (s, 3H)

MS(EI) m/e 307 ($M^+$)

In the same manner as used in EXAMPLE 58, the compounds (n=1) of EXAMPLE 59 to 61, expressed by the general formula (III),were prepared from the compounds of Examples 55, 56, and 57, respectively.

| EXAMPLE | $R_3$ | $^1$H-NMRδ |
|---|---|---|
| 59 | OCONHPh | 8.646(brs, 1H), 7.339(s, 1H), 7.156–7.356(m, 5H), 6.092(s, 1H), 5.573, 5.31(ABq, 2H), 4.359, 4.318(d, d, 2H) 4.267(t, 2H), 2.885(t, 2H) |
| 60 | OCONH i-Pr. | 7.2509(s, 1H), 5.65, 5.3550(ABq, 2H, J=17.2Hz), 4.71(d, 1H), 4.52(d, 1H), 4.3554(t, 2H, J=6.8Hz), 3.7965–3.8806 (m, 1H), 2.9616(t, 2H, J=6.8Hz), 1.1335.(d, 6H) |

-continued

| EXAMPLE | $R_3$ | $^1$H-NMRδ |
|---|---|---|
| 61 | $OCCH_2OCH_3$<br>‖<br>O | used immediately to the next reaction without further purification |

EXAMPLE 62

Preparation of dl-20-desethyl-20-acetoxymethyl camptothecin

With the compound(19 mg, 0.06 mmol) obtained from EXAMPLE 58 and N-(2-aminobenzylidene)-p-toluidine (20 mg, 0.09 mmol), the reaction and work-up was carried out in the same procedure as in EXAMPLE 38 and then, the residue was purified by PTLC with dichloromethane-methanol (20:1) to give the desired compound(9 mg, 36%) as a brown solid.

IR($CHCl_3$) 3400, 1749, 1740, 1654 $cm^{-1}$ $^1$H-NMR (400 MHz, $CDCl_3$+$CD_3OD$=4:1) 8.493 (s, 1H), 8.223 (d, 1H, J=8.4 Hz), 7.988 (d, 1H, J=8.0 Hz), 7.867 (t, 1H, J=7.2 Hz), 7.767 (s, 1H), 7.703 (t, 1H, J=7.2 Hz), 5.697, 5.433 (ABq, 2H, J=16.4 Hz), 5.334 (s, 2H), 4.460 (d, 1H, J=11.2 Hz), 4.330 (d, 1H, J=11.2 Hz), 2.087 (s, 3H)

LRMS(EI) m/e 392 ($M^+$), 331, 320, 305

HRMS m/e ($M^+$) Calcd: 392.1008, Obsd: 392.1006

In the same manner as in EXAMPLE 38, the compounds (R=H and n=1) of EXAMPLE 63 to 65, expressed by the general formula (I), were prepared.

| EXAMPLE | $R_3$ | $^1$H-NMR($CDCl_3$ or $CDCl_3$+$CD_3OD$)δ |
|---|---|---|
| 63 | OCONHPh | 8.501(s, 1H), 8.228(d, 1H, J=8.0Hz), 8.000(d, 1H, J=8.0Hz), 7.879(t, 1H, J=7.8Hz), 7.381(s, 1H), 7.714(t, 1H, J=7.8Hz), 7.361(d, 2H, J=8.0Hz), 7.244(t, 2H, J=7.2Hz), 7.017(t, 1H, J=7.2Hz), 5.705, 5.561(ABq, 2H, J=16.8Hz), 5.328(s, 2H), 4.518(d, 1H, J=11.2Hz), 4.395(d, 1H, J=11.2Hz) |
| 64 | OCONH i-Pr | 9.8022(d, 1H), 8.4071(s, 1H), 8.2465 (d, 1H, J=8.4Hz), 7.9457(d, 1H, J=8.0Hz) 7.8480(t, 1H, J=7.0Hz), 7.7197(s, 1H), 7.6783(t, 1H, J=7.0Hz), 5.7705, 5.4392 (ABq, 2H, J=16.4Hz), 5.4598(s, 2H), 4.4212(d, 1H, J=11.8Hz), 4.2169(d, 1H, J=11.8Hz), 3.7709–3.8068(m, 1H) 1.2605(d, 6H) |
| 65 | $OCCH_2OCH_3$<br>‖<br>O | 8.4077(s, 1H), 8.2476(d, 1H, J=8.7Hz) 7.9451(d, 1H, J=7.1Hz), 7.8447(t, 1H) 7.6998(s, 1H), 7.6787(t, 1H), 5.7736, 5.4860(ABq, 2H, J=16.6Hz), 5.3195(s, 2H), 4.5546(d, 1H, J=11.4Hz), 4.3254 (d, 1H, J=11.4Hz), 4.0714(d, 2H, J=1.0Hz), 3.4257(s, 3H) |

EXAMPLE 66

Preparation of dl-20-desethyl-20-hydroxymethylcamptothecin

A mixture of methanol (6 ml), water (2 ml) and $LiOH.H_2O$ (33 mg, 0.78 mmol) was added to dl-20-desethyl-20-acetoxymethylcamptothecin (140 mg, 0.36 mmol) and the reaction mixture was stirred at room temperature for 1.5 hrs.

The reaction mixture was concentrated under reduced pressure to remove methanol and stirred in an ice bath for 30 mins until the pH of the solution became controlled 3–3.5 with 1N HCl. The solid, so formed, was filtrated, washed with water, isopropanol and ether successively, and under $P_2O_5$, dried in vacuum for 3 hrs to give the desired product (83 mg, 66%) as a yellowish white soild.

IR(KBr) 3436, 1743, 1657 $cm^{-1}$

1H-NMR (400 MHz, $CDCl_3$+DMSO-$d_6$=1:1) δ 8.608 (s, 1H, 8.157 (d, 1H, J=8.0 Hz), 8.106 (s, 1H), 8.050 (d, 1H, J=8.0 Hz), 7.829 (t, 1H, J=7.3 Hz), 7.673 (t, 1H, J=7.3 Hz), 6.741 (s, 1H), 5.441, 5.360 (ABq, 2H, J=16.1 Hz), 5.304 (s, 2H), 3.850–3.89 (m, 1H), 3.681–3.723 (m, 1H)

LRMS(EI) m/e 350 ($M^+$), 320, 306

HRMS m/e ($M^+$) Calcd: 350.0903, Obsd: 350. 0917

In the same manner as in EXAMPLE 39, the compounds (R=H and n=1) of EXAMPLE 67 to 69, expressed by the general formula (I), were prepared.

| EXAMPLE | $R_3$ | $^1$H-NMR ($CDCl_3$) δ |
|---|---|---|
| 67 | $OCH_2OCH_3$ | 8.397(s, 1H), 8.240(d, 1H, J=8.0Hz), 7.939(d, 1H, J=80Hz), 7.838(t, 1H, J=8.0Hz), 7.700(s, 1H), 7.670(t, 1H, J=8.0Hz), 5.713, 5.410(ABq, 2H, J=16.4Hz), 5.313(s, 2H), 4.626, 4.587(ABq, 2H, J=6.8Hz), 4.187(s, 1H), 3.839(d, d, 2H, J=10.4Hz), 3.315(s, 3H) |
| 68 | $OCH_2OEt$ | 8.4192(s, 1H), 8.2621(d, 1H, J=8.4Hz) 7.9602(d, 1H, J=8.4Hz), 7.8588(t, 1H) 7.7240(s, 1H), 7.6917(t, 1H, J=8.0Hz) 5.7287, 5.4221(ABq, 2H, J=16.3Hz), 5.3344(s, 2H), 4.7030, 4.6508(ABq, 2H, J=6.9Hz), 4.2620(s, 1H), 3.8727(q 2H, J=7.0Hz), 3.6212–3.6628(m, 1H), 3.5079–3.5554(m, 1H), 1.2136(t, 3H, J=7.0Hz) |
| 69 | $OCH_2OCH_2CH_2$—$OCH_3$ | 8.3955(s, 1H), 8.1848(d, 1H, J=8.4Hz) 7.9156(d, 1H, J=7.6Hz), 7.8082(t, 1H) 7.7868(s, 1H), 7.6908(t, 1H), 5.6227, |

-continued

| EXAMPLE | $R_3$ | $^1$H-NMR ($CDCl_3$) δ |
|---|---|---|
| | | 5.3642(ABq, 2H, J=16.4Hz), 5.2757(s, 2H), 4.6619(d, 1H, J=6.9Hz), 4.6218 (d, 1H, J=6.9Hz), 3.8422(dd, 2H, J=2, 3, 10.0Hz), 3.6112–3.6380(m, 1H), 3.5719–3.5952(m, 1H), 3.4664–3.4924(m, 2H), 3.3192(s, 3H) |

Experiment 1: Cytotoxicity of the Compounds According to this Invention

1) Materials

Cancer Cell Lines

In the determination of cytotoxicity, the following cell lines, purchased from ATCC (U.S.A.), were used for the experiments as the target organisms: L1210 (ATCC CCL 219), A172 (ATCC CRL 1620), A427 (ATCC HTB 53), A549 (ATCC CCL185), SK-NEP-1 (ATCC HTB 48), CAOV-3 (ATCC HTB 75), HEC-1-B (ATCC HTB 113), DLD-1 (ATCC CCL 221) and KATO-III (ATCC HTB 103), CAKI-2 (ATCC HTB 47).

Preparation of Culture Medium for Cancer Cells

Distilled water was used for the preparation of culture medium. 1 liter of powdered RPMI 1640 medium was dissolved in distilled water and with addition of $NaHCO_3$ (2.0 g), the resulting solution was stirred. After the pH of the solution was adjusted to 6.8 to 7.4, the medium was filtered by 0.22 μm filter. The fetal bovine serum was thermally treated at 56° C. for 30 mins before use.

Reagents

RPMI 1640 culture medium for cancer cells, fetal bovine serum, sodium bicarbonate and trypsin-EDTA buffer were purchased from Gibco Co. And MTT (3,4,5-dimethylthiazol -2-yl) -2,5-diphenyltetrazolium bromide) and sulforhodamine B(SRB) reagent were obtained from Sigma Co. and other general reagents were of G.R. degree.

Test materials Camptothecin, purchased from Sigma Co., was dissolved in dimethylsulfoxide and with addition of Dulbec co's phosphate buffered saline (DPBS), the concentration of dimethylsulfoxide was adjusted to 10% before use. In case of the synthesized test materials dissolved in dimethylsulfoxide, the concentration of dimethylsulfoxide was also adjusted to 10%, while the other packed with DPBS. The final concentration of dimethyl sulfoxide given to cancer cells was adjusted to less than 1%, which had no influence on the growth of cancer cells.

2) Methods

The cancer cells were grown at 37° C., 5% $CO_2$ in RPMI 1640 medium containing 10% (v/v) fetal serum (FBS), 50 μg/ml gentamicin and 2 g/L sodium bicarbonate. (In order to detach anchorage-dependent cell lines grown by adhering to a culture flask) the medium was removed, washed with PBS one time and with addition of 2 to 3 ml of trypsin-EDTA buffer, the monolayers of cancer cells were wholly covered to stand for the time being. Then, a suspension of the cultured cancer cells was prepared, diluted with a medium and inoculated on 96-well plate so that the number of cells may be the same as described in the following Table 1.

20 μl of sample (PBS solution in a control well) was inoculated to 96-well microplate and cultured for 3 days. After cultivation, the anti-neoplastic activites were measured by SRB assay [Test Scheme 1].

As for anchorage-independent cell such as L1210, cells were inoculated so that the number of cell may also be the same as described in the following Table 1. After being cultured for 2 days, the cytotoxicity against the cells were measured by MTT assay [Test Scheme 2].

The optical density was measured using an automatic microplate reader. The concentration of cell-growth inhibition rate by 50% was calculated by $GI_{50}$ (computer PCS version 4.1 by Probit method). As per the experiment one time, the mean of optical density on about 2 to 3 wells was used for the calculation.

TABLE 1

| Cell Line | Origin | Number of inoculated cells per: No. of inoculated cells (well) | Property |
|---|---|---|---|
| (Human) | | | |
| A427 or A549 | Lung | 5,000 | monolayer |
| A172 | CNS | 5,000 | |
| DLD-1 | Colon | 5,000 | |
| HEC-1-b | Endometrium | 5,000 | |
| CAOV-3 | Ovary | 20,000 | |
| SK-NEP-1 or CAKi-2 | Kidney | 20,000 | |
| KATO-III | Stomach | 10,000 | |
| (Mice) | | | |
| L1210 | Leukemia | 14,000 | suspension |

Test Scheme 1: SRB assay

180 μl of cell suspension in medium + 20 μl of sample or PBS
↓
Cultured at 37° C. for 3 days, 5% carbon dioxide.
↓
Precipitated with TCA.
↓
Left at 4° C. for 1 hr.
↓
Washed with distilled water 5 times and dried.
↓
Stained with 0.4% SRB solution for 30 mins.
↓
Washed with 1% HAC solution 5 times.
↓
Dissolved in 10 mM Tris buffer.
↓
Measurement of optical density at 520 nm.
↓
Calculation of $GI_{50}$

| Test Scheme 2: MTT assay |
|---|
| 180 μl of cell suspension in medium + 20 μl of sample or PBS |
| ↓ |
| Cultured at 37° C. for 2 days, 5% carbon dioxide. |
| ↓ |
| Added with 50 μl of MTT solution (2 mg/ml in PBS solution). |
| ↓ |
| Cultured for 4 hrs. |
| ↓ |
| Centrifuged at 2,000 rpm for 10 mins. |
| Removal of supernatant. |
| ↓ |
| Dissolved formazan crystals in DMSO. |
| ↓ |
| Measurement of optical density at 570 nm. |
| ↓ |
| Calculation of $GI_{50}$ |

3) Results

The cytotoxicity results of each cell line were as table 2 and 3:

TABLE 2

| Example NO. | A427 | A172 | DLD-1 | HEC-1-B | CAOV-3 | SK-NEP-1 | KATO III | L1210 | MEAN |
|---|---|---|---|---|---|---|---|---|---|
| 18 | 0.14 | 0.73 | 0.65 | 1.8 | 1.21 | 0.0077 | 8.6 | 0.43 | 1.83 |
| 19 | 0.31 | 1.32 | 0.31 | 4.7 | 0.08 | 0.013 | 0.29 | 0.62 | 1 |
| 26 | 0.23 | 0.15 | 0.17 | 1.37 | 0.09 | 0.0031 | 0.46 | 2.18 | 0.35 |
| 29 | 0.07 | 0.05 | 0.26 | 7.68 | 0.12 | 0.015 | 0.21 | 0.38 | 1.19 |
| 30 | 0.057 | 0.065 | 0.064 | 1.65 | 0.025 | 0.00077 | 0.024 | 0.08 | 0.27 |
| 38 | 0.83 | 1.63 | 0.91 | 20.5 | 2.3 | 0.17 | 3.54 | 2.3 | 4.27 |
| 39 | 0.45 | 1.07 | 0.76 | 1.34 | 0.23 | 0.018 | 0.13 | 0.18 | 0.57 |
| 40 | 2.4 | 1.62 | 2.86 | 2.57 | 1.72 | 0.12 | 0.4 | 2.07 | 1.67 |
| 44 | 2.6 | 0.028 | 0.58 | 10.3 | 1.8 | 3.1 | 2.6 | 3.32 | 3 |
| Camptothecin | 0.032 | 0.017 | 0.047 | 0.081 | 0.02 | 0.00019 | 0.092 | 0.024 | 0.041 |

TABLE 3

| Example NO. | A549 | A172 | DLD-1 | HEC-1-B | CAOV-3 | SK-NEP-1 | KATO III | L1210 | MEAN |
|---|---|---|---|---|---|---|---|---|---|
| 20 | 0.08 | 0.54 | 1.04 | 4.22 | 0.023 | 0.061 | 1.05 | 0.73 | 0.968 |
| 21 | 2.51 | 11.34 | 9.68 | 10.16 | 2.74 | 25.16 | 10.17 | 5.55 | 9.66 |
| 25 | 0.94 | 1.09 | 5.53 | 11.44 | 0.65 | 7.55 | 7.86 | 1.65 | 4.59 |
| 27 | 3.43 | 0.4 | 1.87 | 7.54 | 0.47 | 0.17 | 0.44 | 2.34 | 2.08 |
| 28 | 0.98 | 11.54 | 4.35 | 12.33 | 2.29 | 8.89 | 23.64 | 6.45 | 8.81 |
| 41 | 1.15 | 3.05 | 13.88 | 16.23 | 2.79 | 1.90 | 1.33 | 10.71 | 6.38 |
| 42 | 0.092 | 0.58 | 0.45 | 1.99 | 0.78 | 0.82 | 8.08 | 0.6 | 1.674 |
| 43 | 0.25 | 1.83 | 6.84 | 8.88 | 0.87 | 0.99 | 23.98 | 2.25 | 5.74 |
| 46 | 0.56 | 2.36 | 4.92 | 25.27 | 0.64 | 3.11 | 20.88 | 4.23 | 7.75 |
| 62 | 0.05 | 0.6 | 0.48 | 5.15 | 0.32 | 2.45 | 3.7 | 0.67 | 1.68 |
| 63 | 0.34 | 1.3 | 1.99 | 7.95 | 0.74 | 6.17 | 6.13 | 1.3 | 3.24 |
| 64 | 3.28 | 4.89 | 10.2 | 39.75 | 9.79 | 51.3 | 31.48 | 2.6 | 19.16 |
| 65 | 2.06 | 7.43 | 19.91 | 20.2 | 5.45 | 7.66 | 53.69 | 5.75 | 15.27 |
| 66 | 0.88 | 2.52 | 6.24 | 6.43 | 0.76 | 10.79 | 4.04 | 1.39 | 4.13 |
| 67 | 0.2 | 3.31 | 0.95 | 5.4 | 1.58 | 2.78 | 9.17 | 0.65 | 3.01 |
| 68 | 1.72 | 4.55 | 6.98 | 14.23 | 7.18 | 16.3 | 16.64 | 1.39 | 8.62 |
| 69 | 1.55 | 1.92 | 11.32 | 19.78 | 2.63 | 2.13 | 36.61 | 9.73 | 10.71 |
| Camptothecin | 0.02 | 0.05 | 0.07 | 0.4 | 0.01 | 0.2 | 0.4 | 0.06 | 0.2 |

Experiment 2: Antitumor activities of the Compounds According to this Invention

The antitumor activities may be usually proven by determining tumor growth inhibitory effects on solid tumor and prolongation effects of life span on artificially tumor-bearing animals.

Antitumor activities were measured through the experiments on prolongation effects of life span against L1210-bearing mice and tumor growth inhibitory effects against B16-bearing mice. To evaluate the antitumor activities on L1210 leukemia, a certain number of L1210 cells (in vitro) was intraperitoneally inoculated for propagation and the L1210 cells in ascites were harvested from animals sacrificed by cervical dislocation on 7th day after tumor was implanted.

To investigate tumor growth inhibitory effects against B16 melanoma, a certain number of B16 cells(in vitro) was subcutaneously inoculated for propagation and tumor cells were resected from animals scrificed by cervical dislocation on 14th day after tumor was implanted.

The following is a detailed description of this EXPERIMENT for antitumor activities.

Experimental Animals

Male $BDF_1$ mice, weighing about 20 grams, were used. Animal rooms were controlled at 23±2° C. and 60±5% relative humidity, under HEPA filter, and maintained in specific pathogen free (SPF).

Experiment 2-1: Prolongation Effects of Life Span against L1210-bearing Mice in Accordance with the Compounds of this Invention.

$5\times10^5$ of L1210 leukemia cell, obtained in vitro form, were intraperitoneally inoculated in $BDF_1$ mice for propagation. The L1210 tumor cells in ascites were aseptically harvested from $BDF_1$ mice sacrificed by cervical dislocation on 7th day after tumor implantation.

The tumor cells were passaged at least three times prior to use in the test.

$5\times10^5$ cell were intraperitoneally inoculated into $BDF_1$ mice on day 0 and the sample (0.1 ml/log) were intraperitoneally administration on days 1, 3 and 5. six mice were used for each experimental group.

Antitumor activities were evaluated by the mean survival time of a group of mice and also expressed by the ILS(%) value and the mean animal weights for day 1 and day 5.

Increased Life span (ILS)

ILS(%)={(MST of sample treated group/MST of solvent group)−1}×100

Results

The compound of example 18 given 1st, 3rd and 5th days after the day of tumor inocualtion increased the life span (ILS) of L1210-bearing mice by 33% and 64% at total doses of 10 mg/kg and 50 mg/kg, respectively (Tabel 4).

TABLE 4

Prolongation effects of life aginst L1210 in the compound of example 18

| Compound | Dose (mg/kg) | Survival days MST | Survival days ILS(%) | 30 days survivor | B.W. Change(g) |
|---|---|---|---|---|---|
| Control | | 9.75 | 0 | 0/6 | 0 |
| Compound of example 18 | 10 | 13.00 | 33 | 0/6 | −0.25 |
| Compound of example 18 | 50 | 16.00 | 64 | 0/6 | −0.80 |

The compound of example 26 given 1st, 3rd and 5th days after the day of tumor inoculation increased the life span (ILS) of L1210-bearing mice by 72% and 75% at total doses of 10 mg/kg and 50 mg/kg, respectively (Table 5).

TABLE 5

Prolongation effects of life against L1210 of the compound prepared in example 26

| Compound | Dose (mg/kg) | Survival days MST | Survival days ILS(%) | 30 days survivor | B.W. Change(g) |
|---|---|---|---|---|---|
| Control | | 9.125 | 0 | 0/6 | +1.77 |
| Compound of example 26 | 10 | 15.67 | 72 | 0/6 | −0.09 |
| Compound of example 26 | 50 | 16.00 | 75 | 0/6 | −0.57 |

The compound of example 30 given 1st, 3rd and 5th days after the day of tumor inoculation increased the life span (ILS) of L1210-bearing mice by 42% and 119% at total doses of 10 mg/kg and 50 mg/kg, respectively (Table 6).

TABLE 6

Prolongation effects of life against L1210 of the compound prepared in example 30

| Compound | Dose (mg/kg) | Survival days MST | Survival days ILS(%) | 30 days survivor | B.W. Change(g) |
|---|---|---|---|---|---|
| Control | | 9.125 | 0 | 0/6 | +1.77 |
| Compound of example 30 | 10 | 13.00 | 42 | 0/6 | −0.71 |
| Compound of example 30 | 50 | 20.00 | 119 | 0/6 | −0.57 |

Since the compound of example 30 exhibited better dose dependency and ILS(%) than other compound, the inventor et al. tried to elucidate a higher dose level and amounts showing antitumor activities in experimental animals administered with a higher dose.

When the compound of example 30 was given 1st, 3rd and 5th days after the inoculation at total doses of 8.75, 17.5, 35, 70 and 140 mg/kg, the ILS(%) showed 58.7, 79.7, 92.4, 143 and 110%, respectively (Table 7).

TABLE 7

Prolongation effects of life against L1210 of the compound prepared in example 30 in various dose

| Compound | Dose (mg/kg) | Survival days MST | Survival days ILS(%) | 30 days survivor | B.W. Change(g) |
|---|---|---|---|---|---|
| Control | | 9.875 | 0 | 0/6 | +1.44 |
| Compound of example 30 | 8.75 | 15.67 | 58.7 | 0/6 | +0.7 |
| Compound of example 30 | 17.5 | 17.75 | 29.2 | 0/6 | +0.45 |
| Compound of example 30 | 35 | 19.00 | 92.4 | 0/6 | −0.12 |
| Compound of example 30 | 70 | 24.00 | 143 | 0/6 | −0.79 |
| Compound of example 30 | 140 | 20.75 | 110 | 0/6 | −0.93 |

When the compound of example 30 was given on day 1, 3 and 5 after the tumor inoculation, the maximum ILS of 143% was obtained at total dose of 70 mg/kg.

The antitumor activity of the compound of example 30 against intraperitoneally-implanted L1210 was evaluated in parallel with that of camptothecin as shown in FIG. 1. The compound of example 30 gave higher ILS(%) and wider range where the effect was siginificant.

Experiment 2-2: Tumor Growth Inhibitory Effects on B16-bearing Mice in Accordance with the Compounds of this Invention $10^6$ of B16 melanoma cell, obtained in vitro form, were subcutaneously in $BDF_1$ mice for propagation. The B16 melanomas were transfered on day 14. The fresh tumors except for necrotized center were aseptically resected from tumor-bearing mice sacrificed by cervical dislocation.

The tumor cells were passaged at least injected three times prior to use in the test.

1 g subcutaneously donor tumor to be subcutaneously was homogenized in cold sterilized saline to give a final concentration of 1 g/10 ml. The 1:10 tumor suspension is injected into all $BDF_1$ mice subcutaneously using 0.2 ml/mouse.

The mice were subcutaneously implanted with such homogenized solution and 7 to 8th day after the tumor implantation, the mice having a certain size of tumors were selected for experiments. Each experimental group were administered with the sample (0.1 ml/10 g) on 8th, 12th and 16th day after the inoculation of tumor. Eight mice were used for each experimental group.

Figure 2:
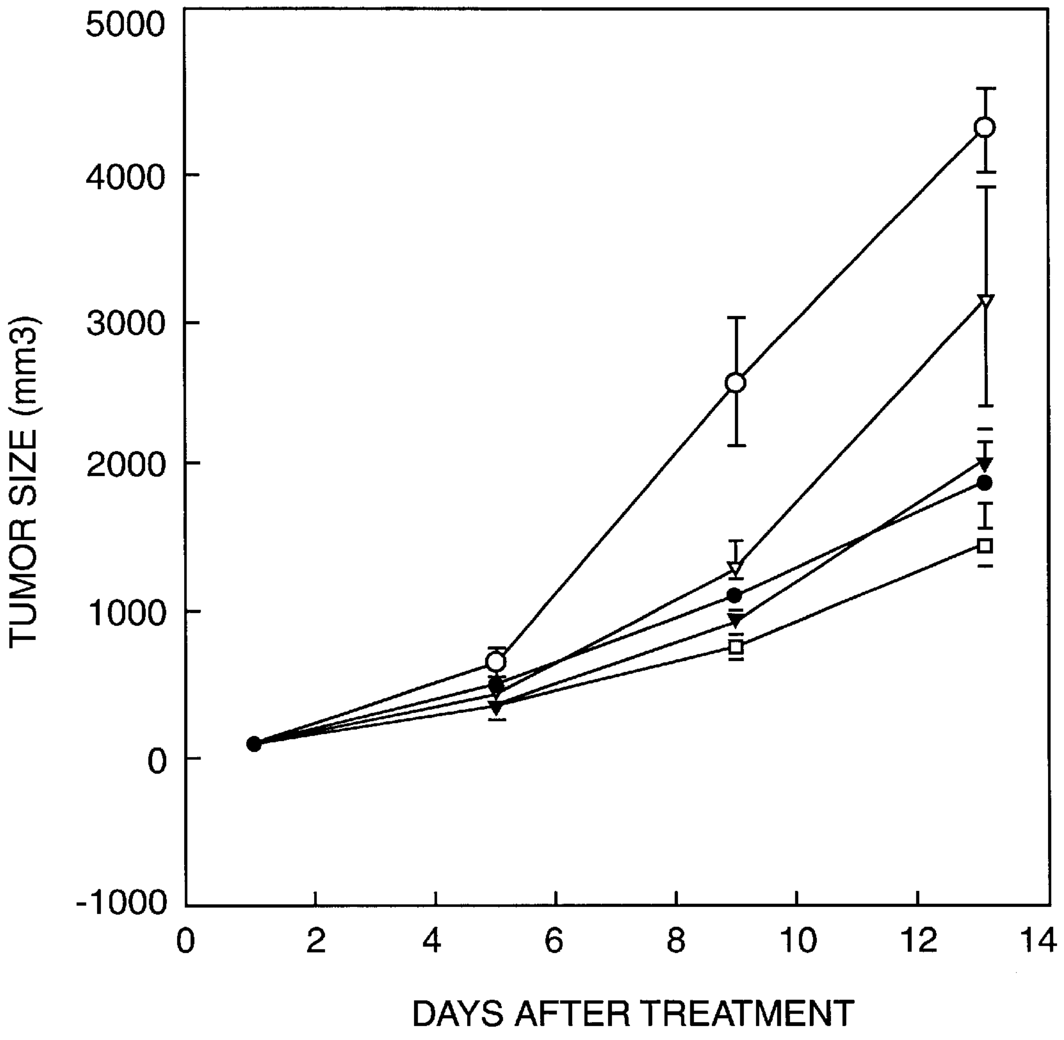
FIG. 2 illustrates the inhibitory effects on mice melanorma cells in accordance with the compound prepared in example 30.

The size of the tumors was calculated by direct measurement of the diameter of the tumors, using the formula.

$$\text{Tumor size}=(a^2b)/2$$

Where b is the largest diameter and a is the diameter perpendicular to b and growth curves were thus obtained. (FIG. 2)

The inhibition rate of tumor growth on the basis of tumor size was calculated according to the formula.

Wherein;

$$IR(\%)=(1-TW_t/TW_c)\times 100$$

$TW_t$ is the mean tumor volume(weight) of sample-treated groups.

$TW_c$ is the mean tumor volume(weight) of control group.

Test Results

When the compound of example 30 was given 8, 12 and 16 days after the tumor inoculation at total doses of 35, 70 and 140 mg/kg , the IR(%) showed 27, 54.8 and 67.72%, respectively (Table 8).

TABLE 8

Tumor growth inhibitory effects against B16 melanoma of the compound prepared in example 30

| | Control | 1. Camptothecin 10 mg/kg | 2. Compound of example 30 35 mg/kg | 3. Compound of example 30 70 mg/kg | 4. Compound of example 30 140 mg/kg |
|---|---|---|---|---|---|
| Tumor size | | | | | |
| day 8 | 87.69 ± 13.58 | 85.95 ± 13.15 | 86.93 ± 11.34 | 86.21 ± 10.12 | 86.94 ± 9.34 |
| day 12 | 598.50 ± 93.59 | 458.56 ± 53.87 | 411.88 ± 71.52 | 320.06 ± 71.79 | 328.98 ± 76.57 |
| day 16 | 2492.75 ± 437.80 | 1035.98 ± 129.36 | 1234.65 ± 182.64 | 870.46 ± 77.27 | 695.75 ± 82.77 |
| day 20 | 4194.83 ± 285.66 | 1775.50 ± 300.91 | 3061.34 ± 752.34 | 1897.88 ± 256.22 | 1353.91 ± 134.36 |
| IR (%) | | 57.8% | 27% | 54.8% | 67.72% |
| Tumor weight | | | | | |
| day 20 | 3.92 ± 0.32 | 1.61 ± 0.30 | 2.34 ± 0.44 | 1.71 ± 0.18 | 1.11 ± 0.21 |
| IR (%) | | 59% | 40% | 56% | 71.6% |

Futher, 20th day after the compound of example 30 was administered, the percentage of IR on the weight of the incised tumor showed 40, 56 and 71.6%, respectively.

The maximum IR of 67.72% was obtained at total dose of 140 mg/kg. The changes in tumor volumes were outlined in FIG. 2. Such results clearly imply that the compound of example 30 has not only better antitumor activity on ascites tumor and solid type tumor, but also less toxicity and a wide range of safety margin, compared with camptothecin.

What is claimed is:

1. A camptothecin compound of the formula I, or a pharmaceutically acceptable salt thereof

I

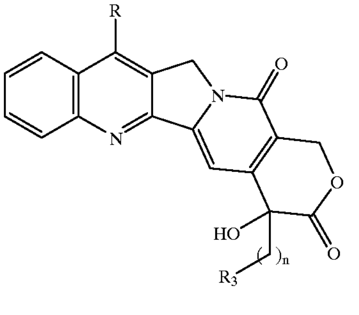

wherein:

R is hydrogen or -$(CH_2)_2$—$NR_1R_2$, where $R_1$ is hydrogen or an amino protecting group and $R_2$ is a lower alkyl, hydroxyethyl or acetoxyethyl group, or $R_1$ and $R_2$, together with the nitrogen atom to which they are attached, form a cyclic moiety;

n is 1 or 2; and $R_3$ is hydrogen or -$OR_4$, where $R_4$ is hydrogen, $COR_5$, $CONHR_6$, or $CH_2OR_7$, where $R_5$ is methyl or $CH_3OCH_2$—, $R_6$ is isopropyl, phenyl or —$CH_2CH_2Cl$ and $R_7$ is methyl, ethyl, or $CH_3OCH_2CH_2$—;

with the provisos that:

R and $R_3$ cannot both be hydrogen;

when n is 2 and R is —$(CH_2)_2$—$N(Cbz)CH_3$, then $R_3$ cannot be hydrogen;

when n is 2 and $R_3$ is OH, then R cannot be hydrogen; and when R is —$CH_2CH_2NHCH_3$, then $R_3$ cannot be hydrogen.

2. An antineoplastic composition containing a camptothecin compound of the formula I, or a pharmaceutically acceptable salt thereof, and a pharmaceutically acceptable carrier

I

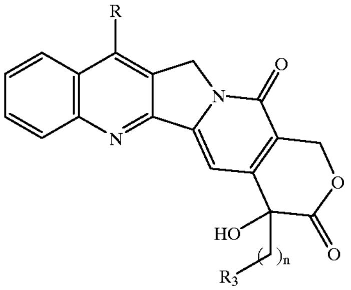

wherein:

R is hydrogen or —$(CH_2)_2$—$NR_1R_2$, where $R_1$ is hydrogen or an amino protecting group and $R_2$ is a lower alkyl, hydroxyethyl or acetoxyethyl group, or $R_1$ and $R_2$, together with the nitrogen atom to which they are attached, form a cyclic moiety;

n is 1 or 2; and $R_3$ is hydrogen or —$OR_4$, where $R_4$ is hydrogen, $COR_5$, $CONHR_6$, or $CH_2OR_7$, where $R_5$ is methyl or $CH_3OCH_2$—, $R_6$ is isopropyl, phenyl or —$CH_2CH_2Cl$ and $R_7$ is methyl, ethyl, or $CH_3OCH_2CH_2$—;

with the provisos that:

R and $R_3$ cannot both be hydrogen;

when n is 2 and R is —$(CH_2)_2$—$N(Cbz)CH_3$, then $R_3$ cannot be hydrogen;

when n is 2 and $R_3$ is OH, then R cannot be hydrogen; and when R is —$CH_2CH_2NHCH_3$, then $R_3$ cannot be hydrogen.

3. A process for manufacturing a compound of the formula I by reacting a compound of the formula II with a compound of the formula III under acidic conditions

II

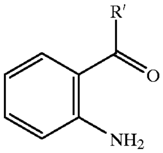

III

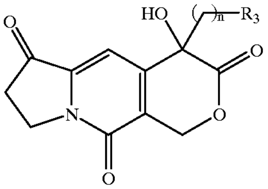

I

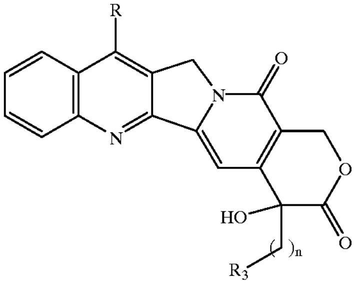

wherein:

R' is hydrogen or $-(CH_2)_2$—$NR_1R_2$, where $R_1$ is an amino protecting group and $R_2$ is a lower alkyl, hydroxyethyl or acetoxyethyl group, or $R_1$ and $R_2$, together with the nitrogen atom to which they are attached, form a cyclic moiety;

P is hydrogen or —$(CH_2)_2$—$NR_1R_2$, where $R_1$ is hydrogen or an amino protecting group and $R_2$ is a lower alkyl, hydroxyethyl or acetoxyethyl group, or $R_1$ and $R_2$, together with the nitrogen atom to which they are attached, form a cyclic moiety;

n is 1 or 2; and $R_3$ is hydrogen or —$OR_4$, where $R_4$ is hydrogen, $COR_5$, $CONHR_6$, or $CH_2OR_7$, where $R_5$ is methyl or $CH_3OCH_2$—, $R_6$ is isopropyl, phenyl or —$CH_2CH_2Cl$ and $R_7$ is methyl, ethyl, or $CH_3OCH_2CH_2$—;

with the provisos that:

R and $R_3$ cannot both be hydrogen;

when n is 2 and R is —$(CH_2)_2$—$N(Cbz)CH_3$, then $R_3$ cannot be hydrogen;

when n is 2 and $R_3$ is OH, then R cannot be hydrogen; and when R is —$CH_2CH_2NHCH_3$, then $R_3$ cannot be hydrogen.

* * * * *

UNITED STATES PATENT AND TRADEMARK OFFICE
CERTIFICATE OF CORRECTION

PATENT NO. : 6,265,413 B1
DATED : July 24, 2001
INVENTOR(S) : Sang Sup Jew et al.

It is certified that error appears in the above-identified patent and that said Letters Patent is hereby corrected as shown below:

Column 32, claim 3,
Delete lines 65-67 and substitute therefor:
-- A process for manufacturing a compound of formula I comprising
(a) reacting a compound of formula II with a compound of formula III for a time and under acidic conditions effective to produce the compound of formula I --.

Column 33 (at the bottom), claim 3,
After the structure for formula I, insert the following two lines:
-- and
(b) recovering the compound of formula I; --.

Column 34, claim 3,
Line 9, "P is hydrogen" should read -- R is hydrogen --.

Signed and Sealed this

Sixteenth Day of April, 2002

Attest:

JAMES E. ROGAN
*Director of the United States Patent and Trademark Office*

*Attesting Officer*